United States Patent
Sekiyama et al.

(10) Patent No.: US 11,306,126 B2
(45) Date of Patent: Apr. 19, 2022

(54) SPIDER SILK PROTEIN FILM, AND METHOD FOR PRODUCING SAME

(71) Applicant: SPIBER INC., Tsuruoka (JP)

(72) Inventors: Kaori Sekiyama, Yamagata (JP); Mizuki Ishikawa, Yamagata (JP); Shinya Murata, Yamagata (JP)

(73) Assignee: SPIBER INC., Yamagata (JP)

( * ) Notice: Subject to any disclaimer, the term of this patent is extended or adjusted under 35 U.S.C. 154(b) by 0 days.

(21) Appl. No.: 16/371,932

(22) Filed: Apr. 1, 2019

(65) Prior Publication Data

US 2019/0300588 A1   Oct. 3, 2019

Related U.S. Application Data

(62) Division of application No. 14/437,704, filed as application No. PCT/JP2013/083753 on Dec. 17, 2013, now Pat. No. 10,329,332.

(30) Foreign Application Priority Data

Dec. 26, 2012 (JP) ................................. 2012-283288
Apr. 26, 2013 (JP) ................................. 2013-093928

(51) Int. Cl.
| | |
|---|---|
| *C07K 14/435* | (2006.01) |
| *C08J 5/18* | (2006.01) |
| *C08L 89/00* | (2006.01) |
| *B29C 39/02* | (2006.01) |
| *B29C 55/02* | (2006.01) |
| *B29C 71/02* | (2006.01) |
| *A61K 38/00* | (2006.01) |
| *B29L 7/00* | (2006.01) |

(52) U.S. Cl.
CPC ........ *C07K 14/43518* (2013.01); *B29C 39/02* (2013.01); *B29C 55/02* (2013.01); *B29C 71/02* (2013.01); *C08J 5/18* (2013.01); *C08L 89/00* (2013.01); *B29K 2089/00* (2013.01); *B29K 2867/003* (2013.01); *B29K 2995/002* (2013.01); *B29L 2007/008* (2013.01); *C08J 2389/00* (2013.01)

(58) Field of Classification Search
CPC ........ A61K 35/646; A61K 9/7007; D01F 4/02
See application file for complete search history.

(56) References Cited

U.S. PATENT DOCUMENTS

| | | | |
|---|---|---|---|
| 5,616,737 A | 4/1997 | Grimmer et al. | |
| 6,316,732 B1* | 11/2001 | Lim | H01L 23/13 174/255 |
| 2003/0183978 A1 | 10/2003 | Asakura | |
| 2004/0228913 A1 | 11/2004 | Kumar et al. | |
| 2006/0229735 A1 | 10/2006 | Roy et al. | |
| 2007/0187862 A1 | 8/2007 | Kaplan et al. | |
| 2007/0196429 A1 | 8/2007 | Scheibel et al. | |
| 2007/0214520 A1 | 9/2007 | Scheibel et al. | |
| 2008/0021553 A1 | 1/2008 | Scheibel et al. | |
| 2008/0176960 A1* | 7/2008 | Tsukada | C12N 5/0068 514/773 |
| 2009/0123967 A1 | 5/2009 | Scheibel | |
| 2009/0234026 A1 | 9/2009 | Kaplan et al. | |
| 2009/0263430 A1 | 10/2009 | Scheibel et al. | |
| 2010/0055438 A1 | 3/2010 | Kaplan et al. | |
| 2010/0196447 A1 | 8/2010 | Kaplan et al. | |
| 2010/0298877 A1 | 11/2010 | Scheibel et al. | |
| 2011/0136669 A1 | 6/2011 | Liebmann et al. | |
| 2011/0223153 A1 | 9/2011 | Lu et al. | |
| 2011/0230911 A1 | 9/2011 | Scheibel et al. | |
| 2012/0306120 A1 | 12/2012 | Li et al. | |
| 2012/0316519 A1* | 12/2012 | Uematsu | A61K 9/7084 604/307 |
| 2013/0165004 A1 | 6/2013 | Kaplan et al. | |
| 2013/0190222 A1 | 7/2013 | Kaplan et al. | |

(Continued)

FOREIGN PATENT DOCUMENTS

| | | |
|---|---|---|
| CN | 101018806 | 8/2007 |
| CN | 101460570 | 6/2009 |
| CN | 102176904 | 9/2011 |

(Continued)

OTHER PUBLICATIONS

Imai et al. (2003) Properties of Poly(ethylene terephthalate)/Layered Silicate Nanocomposites Prepared by Two-Step Polymerization Procedure, Polymer J., vol. 35, No. 3, pp. 230-235.*

International Search Report, dated Mar. 18, 2014; PCT/JP2013/083753 (2 pages).

Rathore et al.: "Self-Assembly of β-Sheets into Nanostructures by Poly(alanine) Segments Incorporated in Multiblock Copolymers Inspired by Spider Silk"; J. Am. Chem. Soc., 2001, vol. 123, No. 22. pp. 5231-5239.

(Continued)

*Primary Examiner* — Manjunath N Rao
*Assistant Examiner* — Samuel W Liu
(74) *Attorney, Agent, or Firm* — Hamre, Schumann, Mueller & Larson, P.C.

(57) ABSTRACT

A film of the present invention contains a polypeptide derived from spider silk proteins. The decomposition temperature of the film is 240 to 260° C. The film absorbs ultraviolet light having a wavelength of 200 to 300 nm and has a light transmittance of 85% or more at a wavelength of 400 to 780 nm. The film is transparent and colorless in a visible light region. A method for producing a film of the present invention includes: dissolving a polypeptide derived from spider silk proteins in a dimethyl sulfoxide solvent to prepare a dope; and cast-molding the dope on a surface of a base. Thus, the present invention provides a spider silk protein film that can be formed easily and has favorable stretchability, and a method for producing the same.

7 Claims, 5 Drawing Sheets
Specification includes a Sequence Listing.

(56) References Cited

U.S. PATENT DOCUMENTS

| | | | |
|---|---|---|---|
| 2013/0243693 A1* | 9/2013 | Omenetto | G02B 5/1809 |
| | | | 424/9.1 |
| 2014/0058066 A1* | 2/2014 | Sekiyama | C07K 14/43518 |
| | | | 530/353 |
| 2014/0093902 A1 | 4/2014 | Omenetto et al. | |
| 2014/0145365 A1 | 5/2014 | Omenetto et al. | |
| 2014/0193460 A1* | 7/2014 | Spector | A61P 31/00 |
| | | | 424/231.1 |
| 2014/0193466 A1 | 7/2014 | Lawrence et al. | |
| 2014/0245923 A1 | 9/2014 | Sugahara et al. | |
| 2015/0038043 A1 | 2/2015 | Kaplan et al. | |
| 2015/0202351 A1* | 7/2015 | Kaplan | A61L 31/10 |
| | | | 607/116 |

FOREIGN PATENT DOCUMENTS

| | | | |
|---|---|---|---|
| CN | 102532295 | 7/2012 | |
| DE | 10313877 B4 * | 12/2006 | D01F 4/02 |
| JP | 2007-515391 | 6/2007 | |
| JP | 2008-506409 | 3/2008 | |
| JP | 2008-507260 | 3/2008 | |
| WO | 2007/025719 | 3/2007 | |
| WO | 2013/065650 | 5/2013 | |
| WO | 2013/065651 | 5/2013 | |

OTHER PUBLICATIONS

Scheibel, et al., "Spider silks: recombinant synthesis, assembly, spinning, and engineering of synthetic proteins", Microbial Cell Factories, Biomed Central, vol. 3, No. 1, Nov. 16, 2004, p. 14.

Extended European Search report issued in corresponding European Patent Application, dated Jun. 2, 2016, 9 pages.

Teramoto, et al., Chemical Modification of Silk Sericin in Lithium Chloride/Dimethyl Sulfoxide Solvent with 4-Cyanophenyl Isoyanate, Biomacromol, vol. 5, 2004, pp. 1392-1398.

Office Action issued in corresponding Chinese Patent Application No. 201380053747.7, dated Sep. 5, 2016, 16 pages with translation.

Osaki S. (2004) Ultraviolet Rays Mechanically Strengthen Spider's Silks, Polymer J., vol. 36, pp. 657-660.

Im, et al. (2016) Gelation Behaviors and Mechanism of silk Fibroin According to the Addition of Nitrate Salt, Internat. J. Mol. Sci., vol. 17, pp. 1-9.

Normandeau, et al. (2014) spider silk protein structure analysis by FTIR and STXM spectromicroscopy techniques, Canadian Young Sci. J. #1.2014, pp. 35-42.

McGhie, et al., (1994) New Internal Structure of Spider Drageline Silk Revealed by Atomic Force Microscopy, Biophys. J., vol. 66, pp. 1209-1212.

Little, et al. (2011) Image contracts immersion method for measuring refractive index applied to spider silks, Optics Exp., vol. 19, pp. 19182-19189.

Cunniff et al. (1994) Mechanical and thermal properties of dragline silk from the spider *Nephila clavipes*, Polymers Adv. Technol., vol. 5, pp. 401-410.

Bonino M.J. (2003) Material Properties of Spider Silk, Themes of MS, University Rochester, pp. 1-107.

Romer, et al., The elaborate structure of spider silk, Structure and function of a natural high performance fiber, Prion 2:4, Oct./Nov./Dec. 2008, pp. 154-161.

* cited by examiner

SPIDER SILK PROTEIN FILM, AND METHOD FOR PRODUCING SAME

TECHNICAL FIELD

The present invention relates to a spider silk protein film capable of being stretched, and a method for producing the same.

BACKGROUND ART

Spiders' threads are also referred to as spider silks, and known to be produced by biosynthetic technologies using natural spider silks as a starting material. Films using spider silk proteins have been proposed in Patent Documents 1-3 below. These documents disclose films formed by dissolving spider silk proteins in a hexafluoroisopropanol (HFIP) solvent.

PRIOR ART DOCUMENTS

Patent Documents

Patent Document 1: JP 2008-507260 A
Patent Document 2: JP 2008-506409 A
Patent Document 3: JP 2007-515391 A

DISCLOSURE OF INVENTION

Problem to be Solved by the Invention

However, there has been a major problem that, if a film or resin is used as a substrate in cast molding, the hexafluoroisopropanol (HFIP) solvent proposed in the conventional methods sometimes dissolves the substrate. Further, since HFIP has a boiling point of 59° C. and has low storage stability, it evaporates at the time of cast molding for film formation, which makes it difficult to form films. Because of this, even the characteristics of spider silk protein films themselves have not been clarified.

In order to solve the above conventional problems, it is an object of the present invention to provide a spider silk protein film that can be formed easily and a method for producing the same that allows easy cast molding without dissolving a substrate made of a film or resin, and to clarify characteristics of the spider silk protein film.

Means for Solving Problem

A spider silk protein film of the present invention is a film that contains a polypeptide derived from spider silk proteins. The decomposition temperature of the film is 240 to 260° C. The film absorbs ultraviolet light having a wavelength of 200 to 300 nm and has a light transmittance of 85% or more at a wavelength of 400 to 780 nm. The film is transparent and colorless in a visible light region.

A method for producing a spider silk protein film of the present invention is a method for producing a film that contains a polypeptide derived from spider silk proteins, the method including: dissolving a polypeptide derived from spider silk proteins in a dimethyl sulfoxide solvent to prepare a dope; and cast-molding the dope on a surface of a base.

Effect of the Invention

The film of the present invention has a decomposition temperature of 240 to 260° C., and has high heat resistance. The film absorbs ultraviolet light having a wavelength of 200 to 300 nm, and has a light transmittance of 85% or more at a wavelength of 400 to 780 nm. The film absorbs ultraviolet light (UV) harmful to the human body, but has a favorable light transmittance at a wavelength of 400 to 780 nm.

This film is transparent and colorless in a visible light region. The above characteristics are useful for optical films and the like. Further, by using dimethyl sulfoxide (hereinafter, also referred to as DMSO) as a solvent, the present invention can provide a spider silk protein film that can be formed easily and has favorable storage stability and a method for producing the same that allows easy cast molding without dissolving a substrate made of a film or resin. DMSO has a melting point of 18.4° C. and a boiling point of 189° C., has high storage stability, is less likely to evaporate at the time of cast molding and assures high safety, thereby allowing formation of films having a uniform thickness and high transparency.

Further, such use of DMSO as a solvent not only enhances the stretchability of the spider silk protein film but also allows the use of resin substrates such as a polyethylene terephthalate (PET) film as a substrate at the time of cast molding.

DESCRIPTION OF THE INVENTION

Figure 1:
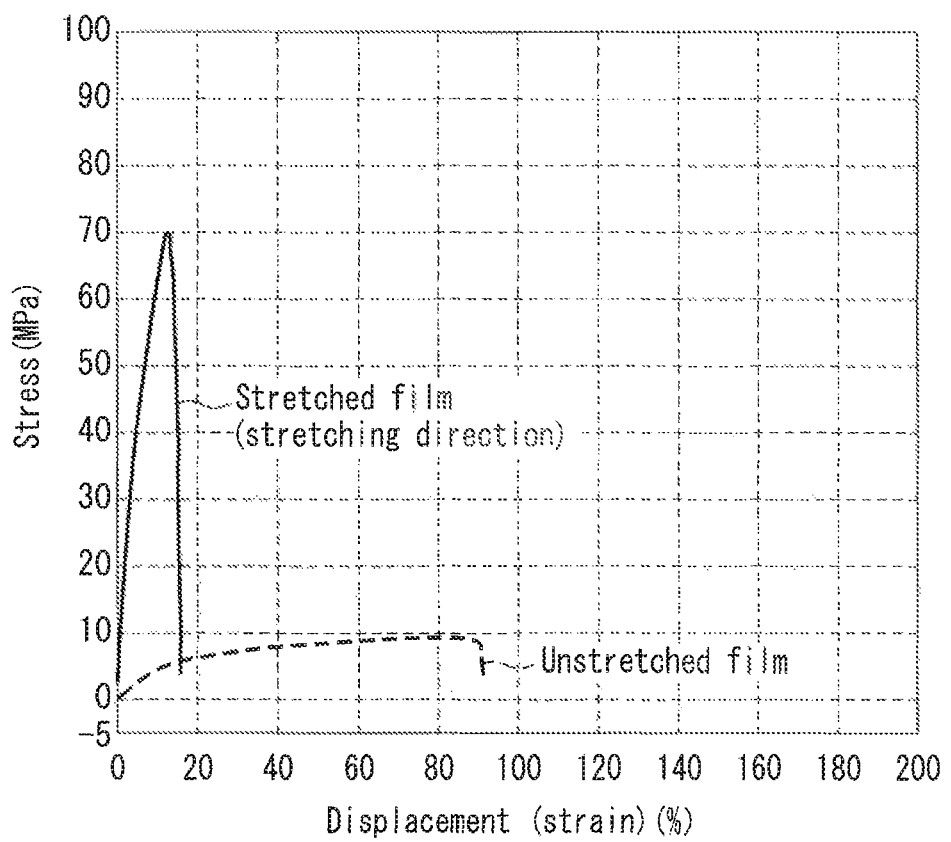
FIG. 1 is a graph showing tensile test measurement of a film in one example of the present invention.

The film of the present invention has a decomposition temperature of 240 to 260° C., and has high heat resistance. The heat resistance can be measured based on the reduction in weight using a thermo-gravimetric/differential thermal analyzer (TG-DTA). Further, according to transmittance measurement, the film absorbs ultraviolet light having a wavelength of 200 to 300 nm, and has a light transmittance of 85% or more at a wavelength of 400 to 780 nm. The film absorbs ultraviolet light (UV) harmful to the human body, but has a favorable light transmittance at a wavelength of 400 to 780 nm. Preferably, the film has a light transmittance of 90% or more at a wavelength of 400 to 780 nm. This film is transparent and colorless in a visible light region. This property is useful for an optical waveguide, an optical film containing a transparent conductive film, and the like.

The spider silk protein film can be stretched. Thermal fixation of the stretched film is preferred because the film can be provided with dimensional stability at ambient temperature (0 to 30° C.). The temperature of the thermal fixation after stretching is preferably 50 to 200° C., and further preferably 80 to 200° C. The time for the thermal fixation is preferably 5 to 600 seconds, and further preferably 20 to 300 seconds.

The refractive index of the spider silk protein film at a wavelength of 590 nm preferably ranges from 1.1 to 1.6, and further preferably ranges from 1.2 to 1.6. The film having a refractive index in this range is useful for an optical waveguide, an optical film containing a transparent conductive film, and the like. The unstretched spider silk protein film has a haze value of preferably 0.5 to 3.0%, and further preferably 1.0 to 2.0%. Within this range, the film can have favorable transparency.

It is preferred that the spider silk protein film has moisture absorbency and has a mass reduction of 4 to 8 weight % in the vicinity of 67 to 94° C. in the thermo-gravimetric/differential thermal analyzer (TG-DTA). This indicates an equilibrium moisture content of the unstretched or stretched film. Further, in the thermo-gravimetric/differential thermal analyzer (TG-DTA), mass reduction is observed in the unstretched film in the vicinity of 175° C., which probably is remaining solvent—DMSO. Since the unstretched film obtained using the DMSO solvent can be stretched easily, it is considered that the remaining DMSO serves as a plasticizer at the time of stretching.

The unstretched film of the spider silk protein film has a maximum stress of 6 to 20 MPa, and further preferably 7 to 18 MPa. The unstretched film has a displacement at rupture point (strain) of 20 to 150%, and further preferably 23 to 95%. Moreover, preferably, the film that has been subjected to thermal fixation after stretching has a maximum stress of 40 MPa or more, preferably 40 to 100 MPa, and further preferably 45 to 75 MPa. The film has a displacement at rupture point (strain) of preferably 10 to 50%, and further preferably 15 to 40%. The maximum stress and the displacement at rupture point (strain) in the above ranges are practical as mechanical characteristics.

In the method of the present invention, a polypeptide derived from spider silk proteins is dissolved in a dimethyl sulfoxide solvent to prepare a dope, and the dope is cast-molded on a surface of a base, followed by drying and/or desolvation. Preferably, the dope has a viscosity of 15 to 80 cP (centipoises) in terms of film formability.

Preferably, the base to be used at the time of the cast molding is a polyethylene terephthalate (PET) film or a release film in which a silicone compound is fixed on a surface of a PET film. These substrates are advantageous in that they are stable with respect to the DMSO solvent, thereby allowing stable cast molding of the dope and easy separation of the resultant cast films. Although the cast film production is possible also using a glass substrate and a metal substrate, their affinity for the dope is so high that the resultant films are difficult to be detached from the substrates. Meanwhile, a fluororesin substrate (e.g., polytetrafluoroethylene) and a polypropylene (PP) film substrate repel the dope, thereby causing separation of liquid from the substrate and making it difficult to produce cast films.

It is preferred that the drying and/or desolvation are performed by at least one means selected from vacuum drying, hot-air drying, air drying, and immersion. The immersion for desolvation of cast film may be performed in water using an alcohol solution such as a lower alcohol with a carbon number of 1 to 5 such as methanol, ethanol, and 2-propanol, or in a mixed solution of water and alcohol. The temperature of the desolvation liquid (coagulation liquid) is preferably 0 to 90° C. Preferably, the solvent is removed as much as possible. In the case of stretching in liquid, desolvation can be performed simultaneously with stretching. Note that the desolvation may be performed after stretching.

The unstretched film after the drying and/or desolvation can be stretched uniaxially or biaxially in water. The biaxial stretching may be either sequential stretching or simultaneous biaxial stretching. Multistage stretching composed of two or more stages may be performed. The stretch ratio is preferably 1.01 to 6 times, and further preferably 1.05 to 4 times in both of the horizontal and vertical directions. Within this range, a balance between the stress and strain can be adjusted easily. The thickness of the unstretched or stretched film is preferably 1 to 1000 µm. The condition of the stretching in water is preferably at a water temperature of 20 to 90° C. The film after the stretching is preferably subjected to thermal fixation by dry heat at 50 to 200° for 5 to 600 seconds. The thermal fixation provides the film with dimensional stability at ambient temperature. Incidentally, the film stretched uniaxially will be a uniaxially-oriented film, and the film stretched biaxially will be a biaxially-oriented film.

In the present invention, DMSO, a polar solvent, is used as a dope of the polypeptide derived from natural spider silk proteins. DMSO has a melting point of 18.4° C. and a boiling point of 189° C. DMSO has a much higher boiling point than hexafluoroisopropanol (HFIP) and hexafluroacetone (HFAc) having boiling points of 59° C. and −26.5° C., respectively, which have been used in conventional methods. Further, in view of the fact that DMSO has been used also in general industrial fields for acrylic fiber polymerization and acrylic fiber spinning solutions, and as solvents for polyimide polymerization, they are low cost substances with proven safety.

The protein of the present invention is a polypeptide derived from spider silk proteins. The polypeptide derived from spider silk proteins is not limited particularly as long as it is derived from natural spider silk proteins or an analog of natural spider silk proteins. In terms of excellent tenacity, the polypeptide derived from spider silk proteins is preferably derived from major dragline silk proteins produced in major ampullate glands of spiders. Examples of the major dragline silk proteins include major ampullate spidroins MaSp1 and MaSp2 derived from *Nephila clavipes*, and ADF3 and ADF4 derived from *Araneus diadematus*, etc.

The recombinant spider silk proteins may be derived from minor dragline silk produced in minor ampullate glands of spiders. Examples of the minor dragline silk proteins include minor ampullate spidroins MiSp1 and MiSp2 derived from *Nephila clavipes*.

Other than these, the recombinant spider silk proteins may be derived from flagelliform silk proteins produced in flagelliform glands of spiders. Examples of the flagelliform silk proteins include flagelliform silk proteins derived from *Nephila clavipes*, etc.

Examples of the polypeptide derived from major dragline silk proteins include a polypeptide containing two or more units of an amino acid sequence represented by the formula 1: REP1-REP2 (1), preferably a polypeptide containing four or more units thereof, and more preferably a polypeptide containing six or more units thereof. In the polypeptide derived from major dragline silk proteins, units of the amino acid sequence represented by the formula 1: REP1-REP2 (1) may be the same or different from each other.

In the formula (1), the REP1 represents polyalanine. In the REP1, the number of alanine residues arranged in succession is preferably 2 or more, more preferably 3 or more, further preferably 4 or more, and particularly preferably 5 or more. Further, in the REP1, the number of alanine residues arranged in succession is preferably 20 or less, more preferably 16 or less, further preferably 12 or less, and particularly preferably 10 or less. In the formula (1), the REP2 is an amino acid sequence composed of 10 to 200 amino acid residues. The total number of glycine, serine, glutamine, proline and alanine residues contained in the amino acid sequence is 40% or more, preferably 50% or more, and more preferably 60% or more with respect to the total number of amino acid residues contained therein.

In the major dragline silk, the REP1 corresponds to a crystal region in a fiber where a crystal β sheet is formed, and the REP2 corresponds to an amorphous region in a fiber where most of the parts lack regular configurations and that has more flexibility. Further, the [REP1-REP2] corresponds to a repetitious region (repetitive sequence) composed of the crystal region and the amorphous region, which is a characteristic sequence of dragline silk proteins.

An example of the polypeptide containing two or more units of the amino acid sequence represented by the formula 1: REP1-REP2 (1) is a recombinant spider silk protein derived from ADF3 having an amino acid sequence represented by any of SEQ ID NO: 1, SEQ ID NO: 2 and SEQ ID NO: 3. The amino acid sequence represented by SEQ ID NO: 1 is an amino acid sequence obtained by the following mutation: in an amino acid sequence of ADF3 to the N-terminal of which has been added an amino acid sequence (SEQ ID NO: 4) composed of a start codon, His 10-tag and HRV3C Protease (Human rhinovirus 3C Protease) recognition site, 1st to 13th repetitive regions are about doubled and the translation ends at the 1154th amino acid residue. The amino acid sequence represented by SEQ ID NO: 2 is an amino acid sequence obtained by adding the amino acid sequence (SEQ ID NO: 4) composed of a start codon, His 10-tag and HRV3C Protease (Human rhinovirus 3C Protease) recognition site, to the N-terminal of a partial amino acid sequence of ADF3 (NCBI Genebank Accession No.: AAC47010, GI: 1263287) obtained from the NCBI database. The amino acid sequence represented by SEQ ID NO: 3 is an amino acid sequence obtained by the following mutation: in an amino acid sequence of ADF3 to the N-terminal of which has been added the amino acid sequence (SEQ ID NO: 4) composed of a start codon, His 10-tag and HRV3C Protease (Human rhinovirus 3C Protease) recognition site, 1st to 13th repetitive regions are about doubled. Further, the polypeptide containing two or more units of the amino acid sequence represented by the formula 1: REP1-REP2 (1) may be a polypeptide that is composed of an amino acid sequence represented by any of SEQ ID NO: 1, SEQ ID NO: 2 and SEQ ID NO: 3 in which one or a plurality of amino acids have been substituted, deleted, inserted and/or added and that has repetitious regions composed of crystal regions and amorphous regions.

In the present invention, "one or a plurality of" refers to 1 to 40, 1 to 35, 1 to 30, 1 to 25, 1 to 20, 1 to 15, 1 to 10, or 1 or a few, for example. Further, in the present invention, "one or a few" refers to 1 to 9, 1 to 8, 1 to 7, 1 to 6, 1 to 5, 1 to 4, 1 to 3, 1 to 2, or 1.

An example of the recombinant spider silk protein derived from minor dragline silk proteins is a polypeptide containing an amino acid sequence represented by the formula 2: REP3 (2). In the formula 2, the REP 3 indicates an amino acid sequence composed of (Gly-Gly-Z)m(Gly-Ala)l(A)r, where Z indicates any one of amino acids, particularly, it is preferably an amino acid selected from the group consisting of Ala, Tyr and Gln. Further, m is preferably 1 to 4, l is preferably 0 to 4, and r is preferably 1 to 6.

Among spider silks, the minor dragline silk is wound spirally from the center of a spider net, and used as a reinforcement of the net and a yarn to wrap a captured prey. The minor dragline silk is inferior to the major dragline silk in tensile strength, but is known to have high stretchability. The reason for this is considered to be as follows: in the minor dragline silk, since many crystal regions are composed of regions where glycine and alanine are arranged alternately in succession, hydrogen bonds of the crystal regions weaken easily as compared with the major dragline silk whose crystal regions are composed only of alanine.

Examples of the recombinant spider silk protein derived from flagelliform silk proteins include a polypeptide containing an amino acid sequence represented by the formula 3: REP4 (3). In the formula 3, the REP 4 indicates an amino acid sequence composed of (SEQ ID NO. 12)n, where Xaa in SEQ ID NO. 12 indicates any one of amino acids, particularly, it is preferably an amino acid selected from the group consisting of Ala, Ser, Tyr and Val. Further, n indicates a number of 4 or larger, preferably 10 or larger, and more preferably 20 or larger.

Among spider silks, the flagelliform silk does not have crystal regions but has repetitious regions composed of amorphous regions, which is a major characteristic of the flagelliform silk. It is considered that since the major dragline silk and the like have repetitious regions composed of crystal regions and amorphous regions, they have both high stress and stretchability. Meanwhile, regarding the flagelliform silk, the stress is inferior to that of the major dragline silk but the stretchability is high. The reason for this is considered to be that the flagelliform silk is composed mostly of amorphous regions.

The polypeptide can be produced using a host that has been transformed by an expression vector containing a gene encoding a polypeptide. A method for producing a gene is not limited particularly, and it may be produced by amplifying a gene encoding a natural spider silk protein from a cell derived from spiders by a polymerase chain reaction (PCR) or the like, and cloning it, or may be synthesized chemically. A method for chemically synthesizing a gene also is not limited particularly, and it can be synthesized as follows, for example: based on information of amino acid sequences of natural spider silk proteins obtained from the NCBI web database or the like, oligonucleotides that have been synthesized automatically with AKTA oligopilot plus 10/100 (GE Healthcare Japan Corporation) are linked by PCR or the like. At this time, in order to facilitate purification and observation of protein, a gene may be synthesized that encodes a protein having the above-described amino acid sequence to the N-terminal of which has been added an amino acid sequence composed of a start codon and His 10-tag. Examples of the expression vector include a plasmid, a phage, a virus and the like that can express protein based on a DNA sequence. The plasmid-type expression vector is not limited particularly as long as it allows a target gene to be expressed in a host cell and it can amplify itself. For example, in the case of using *Escherichia coli* Rosetta (DE3) as a host, a pET22b(+) plasmid vector, a pCold plasmid vector and the like can be used. Among these, in terms of productivity of protein, it is preferable to use the pET22b(+) plasmid vector. Examples of the host include animal cells, plant cells, microbes, etc.

When the dope of the present invention is 100 mass %, the concentration of a solute (the polypeptide derived from natural spider silk proteins) is preferably 3 to 50 mass %, more preferably 3.5 to 35 mass %, and particularly preferably 4.2 to 15.8 mass %.

After removing dusts and bubbles, the viscosity of the dope is preferably 15 to 80 cP (centipoises), and further preferably 20 to 70 cP. The film cast molding is performed using the dope of this viscosity. Specifically, preferably on a PET film substrate on which a release layer is formed, the dope is cast so as to produce a wet film having a constant thickness using a film thickness control means such as an applicator, a knife coater, and a bar coater. In the case of a dry system, the solvent is dried, and the obtained film is subjected to drying and/or desolvation by vacuum drying, hot-air drying, air drying, etc. In the case of a wet system, the cast film is immersed into a desolvation bath (also referred to as a coagulation bath) to remove the solvent. Then, the film may be stretched as described above.

A color film also can be produced in the present invention. First, a colorant such as a dye is dissolved or dispersed in DMSO to prepare a DMSO coloring liquid. The colorant dissolves or disperses in DMSO easily. The coloring liquid is added to the dope, or the dope is added to the coloring liquid and mixed together, followed by film cast molding in the same manner as described above. Then, the resultant is subjected to drying and/or desolvation, and may be formed into an unstretched or stretched color film. The obtained color film can be applied to a reflector, a marker, an ultraviolet preventing film, a slit yarn, etc.

EXAMPLES

Hereinafter, the present invention will be described in further detail by way of examples. Note that the present invention is not limited to the following examples.

<Various Measurement Methods>

(1) Light Transmittance

A UV-Vis-NIR spectrophotometer manufactured by Shimadzu Corporation was used.

(2) Thermal Analysis

A Thermo-Gravimetric/Differential Thermal Analyzer (TG-DTA) manufactured by Seiko Instruments Inc. was used.

(3) Refractive Index

In accordance with JIS K 7142, an Abbe Refractometer 2T manufactured by ATAGO Co., Ltd. was used to measure refractive index under the following conditions: measurement temperature: 23° C.; light source: Na lamp (D beam/589 nm); the number of measurements: 3; contact liquid: diiodomethane.

(4) Viscosity

An EMS machine manufactured by Kyoto Electronics Manufacturing Co., Ltd. was used.

(5) Tensile Test

A tensile testing machine manufactured by Shimadzu Corporation was used.

(6) Film Thickness Measurement

A digital outside micrometer manufactured by Niigata Seiki Co., Ltd. was used.

(7) Measurement of Remaining Amount of Solvent

As an internal standard, 1,2-dichloroethane-formic acid solution at a concentration of 3,100 ppm (0.00310 mg/ml) was prepared. 500 µl of a protein solution (0.1 g of the protein film was dissolved in 10 ml of formic acid) and 5000 of an internal standard solution were mixed. Further, an acetonitrile deuterated solvent for H-NMR measurement was added to the mixed solution in an amount approximately equivalent to that of the mixture solution so as to dilute the solution to about two times, and then H-NMR measurement was performed (NMR model: JNM-ECX 100 manufactured by JOEL Ltd.). The H-NMR integrated intensity of 1,2-dichloroethane (internal standard sample) was compared with the H-NMR integrated intensity of DMSO. A calibration curve was formed by preparing a DMSO-formic acid solution at 3 ppm to 3000 ppm and following the above protocol. By comparison with the calibration curve, the concentration of DMSO in the protein solution was calculated. A nuclear magnetic resonator (NMR) manufactured by JOEL Ltd. was used for the measurement of the concentration of DMSO.

Examples 1-4, Comparative Example 1

1. Preparation of Polypeptide Derived from Spider Silk Proteins

<Gene Synthesis>

(1) Gene Synthesis of ADF3Kai

A partial amino acid sequence of ADF3 (GI: 1263287), which is one of two principal dragline silk proteins of *Araneus diadematus*, was obtained from the NCBI web database, and synthesis of a gene encoding an amino acid sequence (SEQ ID NO: 2) was outsourced to GenScript, Inc. The amino acid sequence (SEQ ID NO: 2) is an amino acid sequence obtained by adding an amino acid sequence (SEQ ID NO: 4) composed of a start codon, His 10-tag and HRV3C Protease (Human rhinovirus 3C Protease) recognition site, to the N-terminal of said partial amino acid sequence of ADF3. Consequently, a pUC57 vector to which a gene of ADF3Kai having a base sequence represented by SEQ ID NO: 5 had been introduced was obtained (having an Nde I site immediately upstream of 5' terminal of the gene and an Xba I site immediately downstream of 5' terminal thereof). Thereafter, the gene was subjected to a restriction enzyme treatment with Nde I and EcoR I, and recombined into a pET22b(+) expression vector.

(2) Gene Synthesis of ADF3Kai-Large

The half of the gene sequence of ADF3Kai on the 5' side (hereinafter, referred to as a sequence A) was amplified by the PCR reaction using ADF3Kai as a template, and a T7 promoter primer (SEQ ID NO: 8) and a Rep Xba I primer (SEQ ID NO: 9). The obtained DNA fragment of the sequence A was recombined into a pUC118 vector that in advance had been subjected to the restriction enzyme treatment with Nde I and Xba I using a Mighty Cloning Kit (manufactured by TAKARABIO INC.). Similarly, the half of the gene sequence of ADF3Kai on the 3' side (hereinafter, referred to as a sequence B) was amplified by the PCR reaction using ADF3Kai as a template, and an Xba I Rep primer (SEQ ID NO: 10) and a T7 terminator primer (SEQ ID NO: 11). The obtained DNA fragment of the sequence B was recombined into a pUC118 vector that in advance had been subjected to the restriction enzyme treatment with Xba I and EcoR I using the Mighty Cloning Kit (manufactured by TAKARA BIO INC.). The pUC118 vector to which the sequence A had been introduced and the pUC118 vector to which the sequence B had been introduced were subjected to the restriction enzyme treatment with Nde I, Xba I and Xba I, EcoR I, respectively, and target DNA fragments of the sequences A and B were purified by gel cut. The DNA fragments A, B and the pET22b(+) that in advance had been subjected to the restriction enzyme treatment with Nde I and EcoR I were subjected to a ligation reaction and transformed into *Escherichia coli* DH5α. After confirmation of the insertion of the target DNA fragments by a colony PCR using a T7 promoter primer and a T7 terminator primer, plasmid was extracted from a colony where a target band size (3.6 kbp) was obtained, and the entire base sequence was checked by a sequence reaction using a 3130×1 Genetic Analyzer (Applied Biosystems). Consequently, the construction of a gene of ADF3Kai-Large represented by SEQ ID NO: 6 was confirmed. The amino acid sequence of ADF3Kai-Large is as represented by SEQ ID NO: 3.

(3) Gene Synthesis of ADF3Kai-Large-NRSH1

With a pET22b(+) vector to which the gene of ADF3Kai-Large obtained above had been introduced used as a template, through site-directed mutagenesis using a PrimeSTAR Mutagenesis Basal Kit (manufactured by TAKARA BIO INC.), a codon GGC corresponding to the 1155th amino acid residue, i.e., glycine (Gly), in the amino acid sequence of ADF3Kai-Large (SEQ ID NO: 3) was mutated into a stop codon TAA, and a gene of ADF3Kai-Large-NRSH1 represented by SEQ ID NO: 7 was constructed on the pET22b(+). The accuracy of the introduction of the mutation was checked by the sequence reaction using the 3130×1 Genetic Analyzer (Applied Biosystems). The amino acid sequence of ADF3Kai-Large-NRSH1 is as represented by SEQ ID NO: 1.

<Expression of Protein>

The pET22b(+) expression vector containing the gene sequence of ADF3Kai-Large-NRSH1 was transformed into *Escherichia coli* Rosetta (DE3). The obtained single colony was incubated for 15 hours in 2 mL of an LB culture medium containing ampicillin. Thereafter, 1.4 ml of said culture solution was added to 140 mL of an LB culture medium containing ampicillin, and incubated to an $OD_{600}$ of 3.5 under the conditions of 37° C. and 200 rpm. Next, the culture solution with the $OD_{600}$ of 3.5 was added to 7 L of a 2xYT culture medium containing ampicillin, together with 140 mL of 50% glucose, and incubated further to the Mao of 4.0. Thereafter, isopropyl-β-thiogalactopyranoside (IPTG) was added to the obtained culture solution with the $OD_{600}$ of 4.0 so that the final concentration would be 0.5 mM, thereby inducing the expression of protein. After a lapse of two hours from the addition of IPTG, the culture solution was centrifuged and bacterial cells were collected. Protein solutions prepared from the bacterial cells before the addition of IPTG and after the addition of IPTG were each electrophoresed in a polyacrylamide gel. Consequently, a target band size (about 101.1 kDa) was observed with the addition of IPTG, and the expression of the target protein was confirmed.

Purification (1) About 50 g of bacteria cells of the *Escherichia coli* expressing the ADF3Kai-Large-NRSH1 protein and 300 ml of a buffer solution AI (20 mM Tris-HCl, pH 7.4) were placed in a centrifuge tube (1000 ml). After dispersing the bacteria cells with a mixer ("T18 basic ULTRA TURRAX" manufactured by IKA, level 2), the dispersion was centrifuged (11,000 g, 10 minutes, room temperature) with a centrifuge ("Model 7000" manufactured by Kubota Corporation), and a supernatant was discarded.

(2) To a precipitate (bacteria cells) obtained by the centrifugation, 300 ml of the buffer solution AI and 3 ml of 0.1 M PMSF (dissolved by isopropanol) were added. After dispersing the precipitate for 3 minutes with the above mixer (level 2) manufactured by IKA, the bacteria cells were disrupted repeatedly for three times using a high-pressure homogenizer ("Panda Plus 2000" manufactured by GEA Niro Soavi).

(3) To the disrupted bacterial cells, 300 mL of a buffer solution B (50 mM Tris-HCL, 100 mM NaCl, pH 7.0) containing 3 w/v % of SDS was added. After dispersing well the bacterial cells with the above mixer (level 2) manufactured by IKA, the dispersion was stirred for 60 minutes with a shaker (manufactured by TAITEC CORPORATION, 200 rpm, 37° C.). Thereafter, the stirred dispersion was centrifuged (11,000 g, 30 minutes, room temperature) with the above centrifuge manufactured by Kubota Corporation, and a supernatant was discarded, whereby SDS washing granules (precipitate) were obtained.

(4) The SDS washing granules were suspended in a DMSO solution containing 1M lithium chloride so that the concentration would be 100 mg/mL, and heat-treated for 1 hour at 80° C. Thereafter, the heated suspension was centrifuged (11,000 g, 30 minutes, room temperature) with the above centrifuge manufactured by Kubota Corporation, and the supernatant was collected.

(5) Ethanol in an amount three times greater than that of the collected supernatant was prepared. The collected supernatant was added to the ethanol, and left to stand still for 1 hour at room temperature. Thereafter, the resultant was centrifuged (11,000 g, 30 minutes, room temperature) with the above centrifuge manufactured by Kubota Corporation to collect aggregated protein. Next, a process of washing aggregated protein using pure water and a process of collecting aggregated protein by centrifugation were repeated three times, and thereafter water was removed by a freeze dryer to collect freeze-dried powder. The purification degree of the target protein ADF3Kai-Large-NRSH1 (about 56.1 kDa) in the obtained freeze-dried powder was checked by analyzing images of the results of polyacrylamide gel electrophoresis (CBB staining) of said protein powder using Totallab (nonlinear dynamics Ltd.). As a result, the purification degree of ADF3Kai-Large-NRSH1 was about 85%.

2. Adjustment of Dope

A dope was prepared by dissolving the spider silk protein in a DMSO solvent so that the concentration of the protein would be 5.98 mass %. After 3 hours of dissolution using a shaker, dusts and bubbles were removed from the dope. The solution viscosity of the dope was 23.5 cP (centipoises).

3. Film Cast Molding

In Example 1, a release film (manufactured by Mitsui Chemicals Tohcello, Inc., product number "SP-PET-01-75-BU"), in which a silicone compound is fixed on a surface of a 75 μm-thick polyethylene terephthalate (PET) film, was used as a substrate. The dope was cast-molded on the surface of the substrate using a film applicator (150 mm, with a micrometer, manufactured by MTI Corporation). Thereby, a wet film was produced. In the other Examples and Comparative Examples, wet films were produced in the same manner as in Example 1 using substrates shown in Table 1.

4. Drying

After 16 hours of standing at 60° C., each film was left to stand still for another 16 hours in a vacuum dryer at 60° C. to be dried. The unstretched spider silk protein film thus obtained was detached from the substrate. If the film could not be detached in air, it was immersed in water to be detached.

Table 1 summarizes the results of the unstretched films obtained by the above-described manner. The evaluations in Table 1 are based on the following.

<Casting Property>

A: The casting property with respect to the substrate is favorable: the dope can be cast in a uniform thickness.

B: The casting property with respect to the substrate is slightly unsatisfactory: the thickness of the dope is uneven.

C: The casting property is poor: the dope is repelled from the substrate.

<Detachability of Film>

A: The film can be detached in air favorably.

B: The film is difficult to be detached in air, but can be detached in water.

C: The film cannot be detached even in water.

TABLE 1

|  | Type of substrate | Casting property | Detachability | Remarks |
|---|---|---|---|---|
| Example 1 | PET film (75 μm) + silicone releasing treatment | A | A | A transparent and colorless film having a thickness of 33.6 μm without scratches was obtained |
| Example 2 | PET (100 μm) film | A | A | Same as above |
| Example 3 | Glass plate | A | B | A film obtained could be detached in water but got scratches at the time of the detachment. |
| Example 4 | Acrylic plate | B | B | Same as above |
| Comparative Example 1 | Copper plate | A | C | A film obtained could not be detached even in water. |

As described above, in Examples 1 and 2 of the present invention, favorable unstretched films were obtained because the PET film or the film in which a silicone releasing thin film was formed on a PET film was used as the substrate. Although there were some problems in detachability in Example 3 and in the casting property and detachability in Example 4, films could be formed. On the other hand, in Comparative Example 1, a film could be formed but the detachability was poor.

Examples 5-8

The unstretched film obtained in Example 1 was stretched uniaxially in water. Table 2 shows the various conditions and results.

TABLE 2

|  | Temperature of water (° C.) | Length of film before stretching | Length at the time of rupture (mm) | Maximum stretch ratio (times) |
|---|---|---|---|---|
| Example 5 | 5 | 30 | 40 | 1.3 |
| Example 6 | 25 | 30 | 60 | 2.0 |
| Example 7 | 48 | 30 | 80 | 2.6 |
| Example 8 | 79 | 30 | 50 | 1.6 |

As can be seen from Table 2, in the range of 5 to 79° C., the film could be stretched in water. In the range of 25 to 48° C., the stretch ratio of two times or more was achieved.

Example 9

It was found that the film obtained by uniaxially stretching the unstretched film of Example 1 in water shrank at room temperature of 25° C. In order to stop such shrinkage, the film was subjected to thermal fixation. Table 3 shows the various conditions and results.

TABLE 3

|  | Conditions of stretching | | | Shrinkage ratio (%) |
|---|---|---|---|---|
|  | Temperature of water (° C.) | Stretch ratio (times) | Conditions of thermal fixation | |
| Example 9 | 45 | 2.0 | Performing heat treatment for 180 seconds using a hot-air dryer at 55° C. (distance between film and dryer was 160 mm) | 0 |

As can be seen from Table 3, the shrinkage could be stopped by thermal fixation after stretching.

Examples 10-11

An unstretched film was produced in the same manner as in Example 1. The film had a thickness of 23.4 μm (Example 10). This unstretched film was stretched uniaxially to 1.5 times in water at 50° C. The film had a thickness of 19.8 μm (Example 11). Table 4 below shows the results of tensile test on the respective films obtained. The tensile test was performed under environments of 25° C. and 60% RH (humidity). The values of the uniaxially-stretched film of Example 11 shown in Table 4 are values in the stretching direction. FIG. 1 summarizes the data.

TABLE 4

|  | Example 10 (unstretched film) | Example 11 (uniaxially-stretched film) |
|---|---|---|
| Maximum stress (calculated in all areas) (MPa) | 9.08 | 70.28 |
| Displacement at rupture point (strain), last 100 msec (%) | 90.62 | 15.21 |
| Elastic modulus, maximum inclination, 2 points (MPa) | 214.63 | 1445.52 |
| Maximum test force (calculated in all areas) (N) | 2.83 | 14.48 |
| Distance between grippers (mm) | 20.00 | 20.00 |
| Thickness (μm) | 31.2 | 20.6 |
| Width (mm) | 10.00 | 10.00 |

Figure 2:
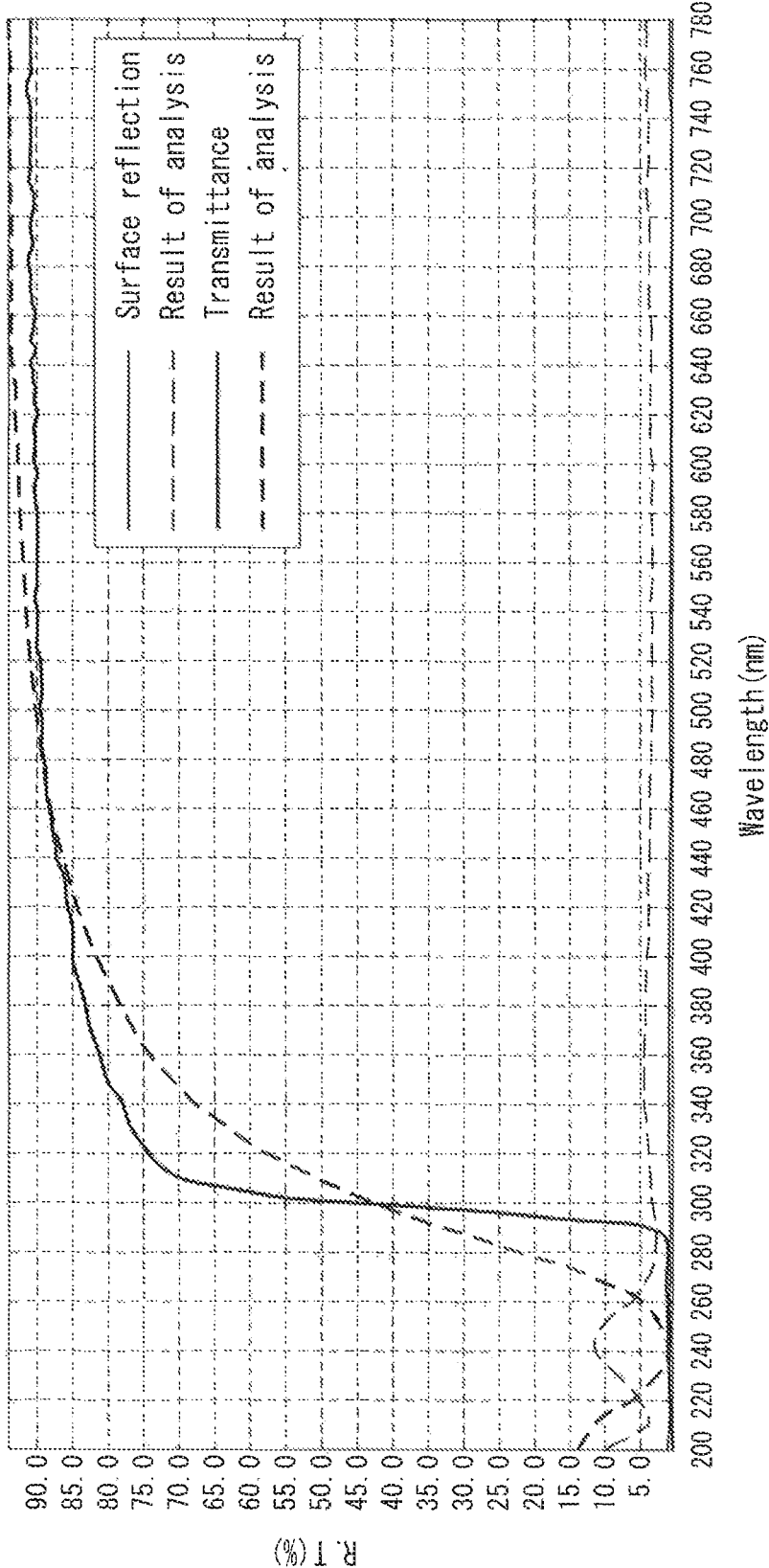
FIG. 2 is a graph showing light transmittance measurement of an unstretched film in one example of the present invention.
Figure 3:
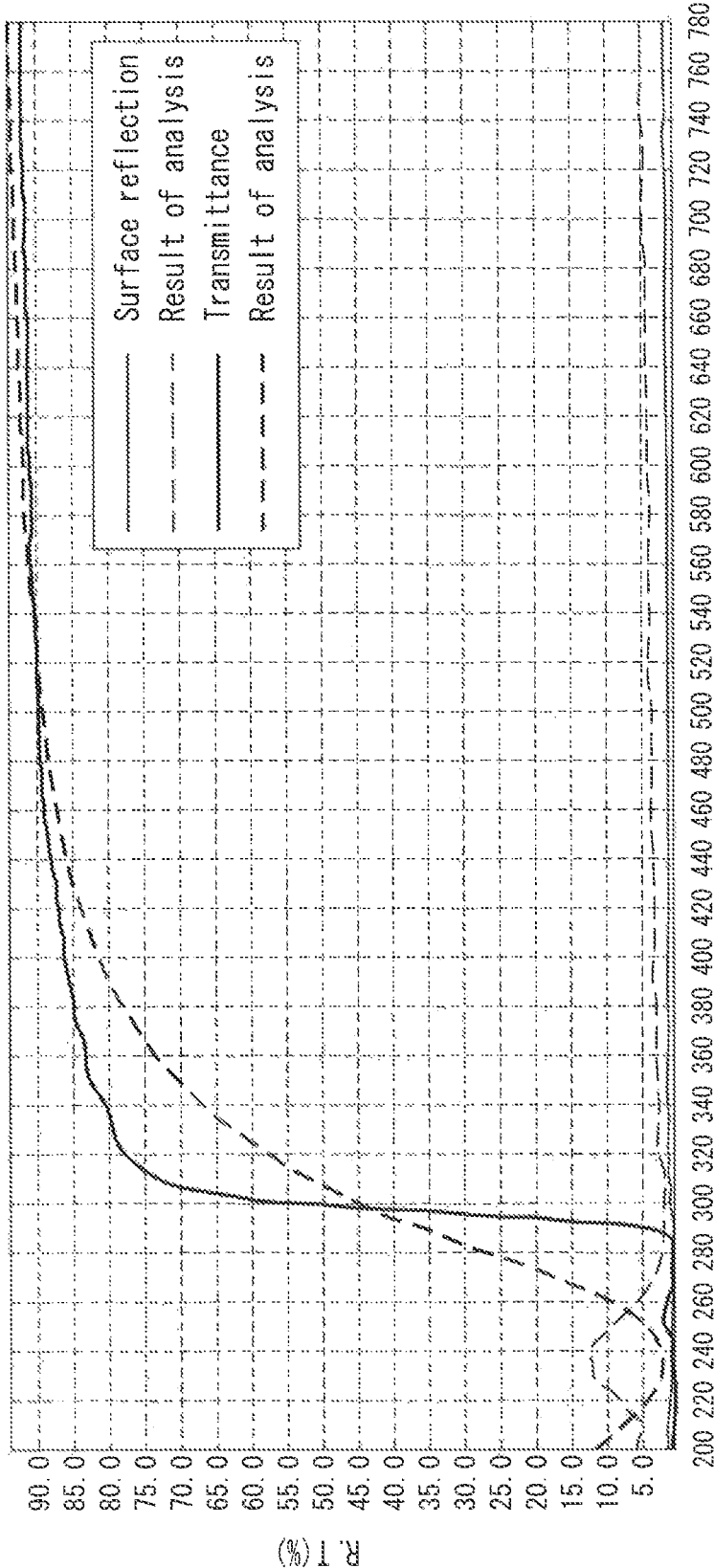
FIG. 3 is a graph showing light transmittance measurement of a stretched film in one example of the present invention.

Both of the unstretched films obtained in Examples 1 and 10 had a refractive index $n_D$ of 1.556. FIGS. 2 and 3 show graphs of light transmittance measurement. FIG. 2 is a graph showing the light transmittance measurement of the film of Example 10, and FIG. 3 is a graph showing the light transmittance measurement of the film of Example 11. The films absorbed ultraviolet light having a wavelength of 200 to 300 nm, and exhibited a light transmittance of 85% or more at a wavelength of 400 to 780 nm.

Figure 4:
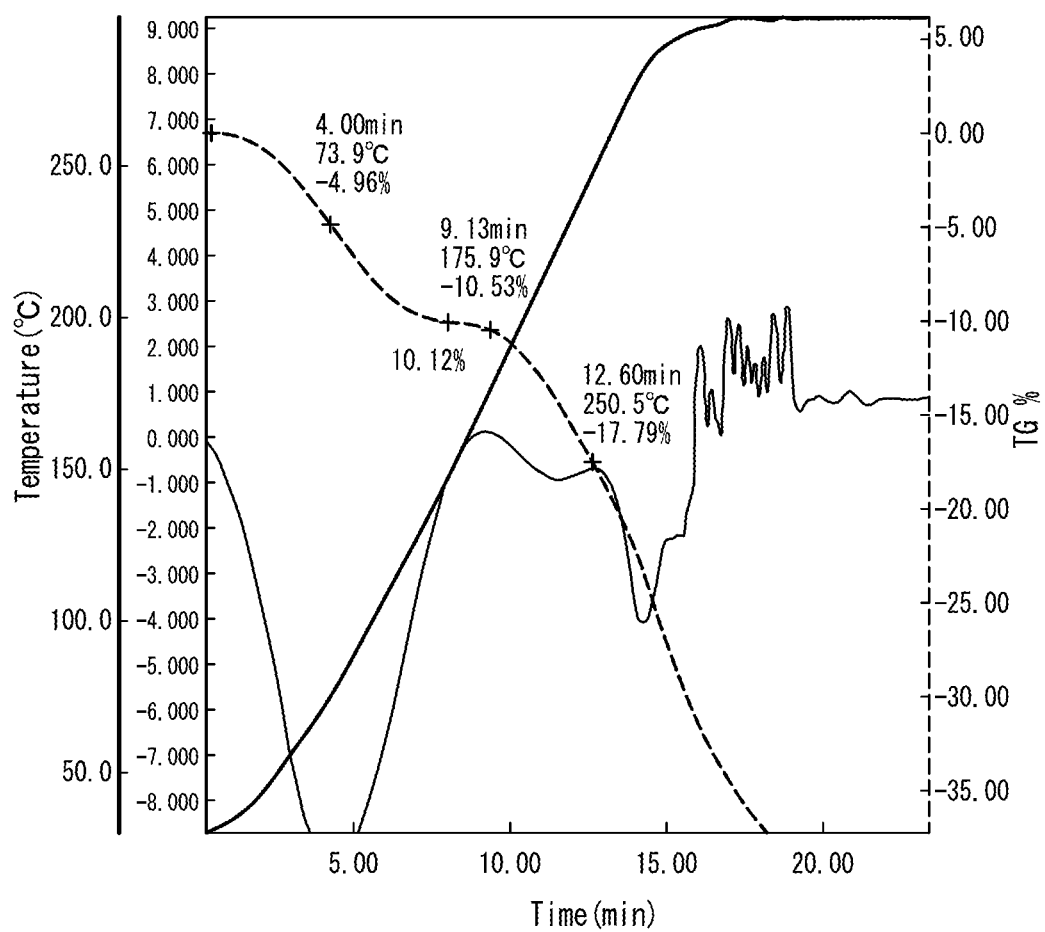
FIG. 4 is a graph showing thermogravimetric measurement of a film in one example of the present invention.
Figure 5:
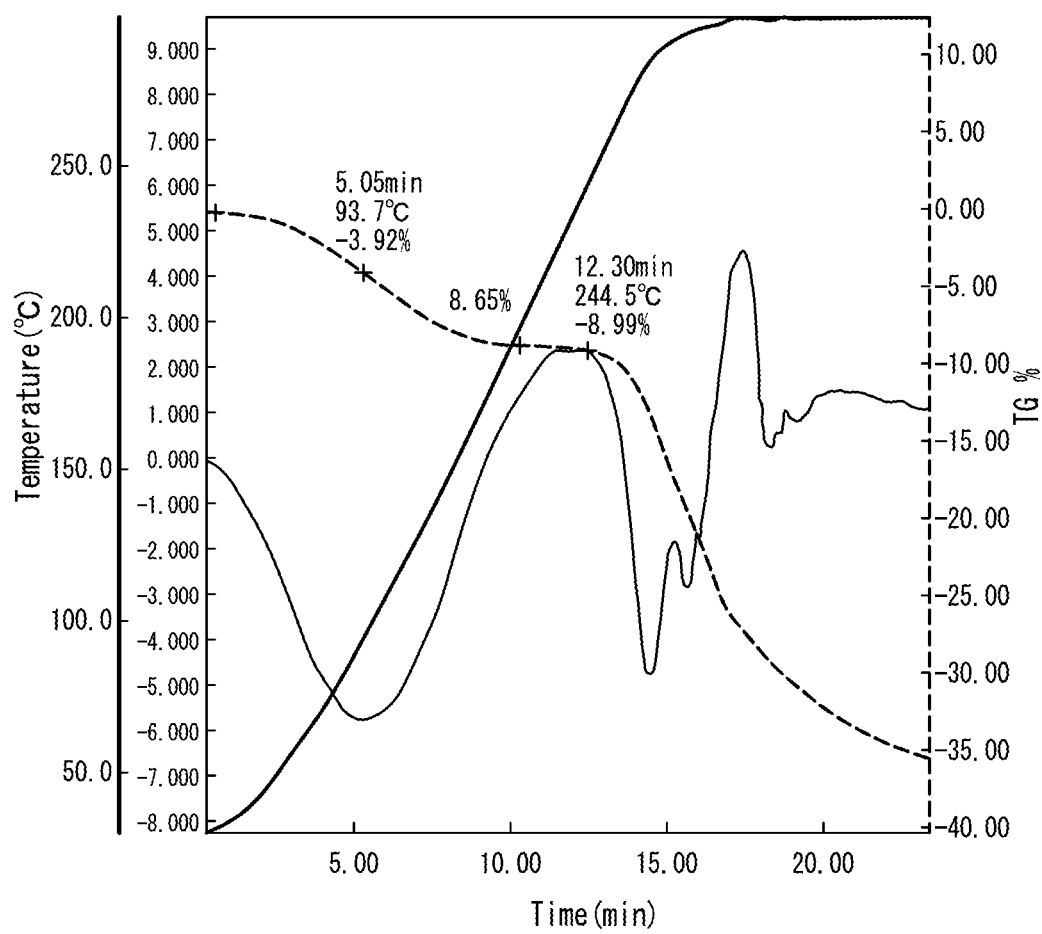
FIG. 5 is a graph showing thermogravimetric measurement of a film in one example of the present invention.

FIG. 4 is a graph showing thermal analysis measurement of the film of Example 10, and FIG. 5 is a graph showing thermal analysis measurement of the film of Example 11. Both of the films had a mass reduction of 4 to 8 mass % in the vicinity of 67 to 94° C., which probably is the amount of equilibrium moisture absorbed. It also was found that the decomposition temperature of the film was present in the vicinity of 240 to 260° C. Further, the unstretched film of Example 10 had a mass reduction also in the vicinity of 175° C., which probably is the remaining solvent—DMSO.

Example 12

The unstretched film obtained in Example 1 (50 mm in length, 50 mm in width and 32 μm in thickness) was stretched biaxially to 1.26 times in an X-axis direction and 1.26 times in a Y-axis direction simultaneously under environments of 78 to 80 RH % (humidity) and 24° C. (temperature). The tensile speed was 30 mm/min. A film biaxial stretching machine manufactured by Imoto Machinery Co., Ltd. was used as a stretching machine. Simultaneous biaxial stretching was possible.

Comparative Example 2

Hexafluoroisopropanol (HFIP) was used as a solvent, and the same spider silk protein as that of Example 1 was used. A dope was prepared by dissolving the spider silk protein in the HFIP solvent so that the concentration of the protein would be 5.98 mass %. The test was performed in the same manner as in Example 1 except that the same substrates as those of Examples 1 and 2 were used as the casting substrates. As a result, the PET substrates were swelled and dissolved by HFIP, and could no longer be used as the substrates.

To cope with this, a glass substrate was used for casting. However, the resultant film was difficult to be detached from the substrate, and needed to be detached gradually in water with great effort to obtain an unstretched film. A sample 20 mm in length and 40 mm in width of this unstretched film was set in a manual uniaxial stretching machine (manufactured by Imoto Machinery Co., Ltd.) (the distance between grippers: 20 mm) and pulled in hot water at 50° C. As a result, the film dissolved partially and tore, and hence stretching was impossible.

Example 13

In this example, methods of removing the solvent DMSO were tested. The desolvation shown in Table 5 was performed using the unstretched film (thickness: 55.2 μm) obtained in Example 1. The remaining amount of DMSO was quantified using NMR. Table 5 shows the results.

TABLE 5

| No. | Conditions of removal of DMSO | Remaining amount of DMSO in film (mass %) |
| --- | --- | --- |
| 1 | Unstretched film, untreated | 11.2 |
| 2 | Vacuum drying at 60° C., 24 hours | 11.1 |
| 3 | Vacuum drying at 60° C., 48 hours | 11.0 |
| 4 | 100% methanol, 25° C., 24 hours | 0.03 |
| 5 | 100% methanol, 25° C., 48 hours | Not detected |
| 6 | 50% methanol/aqueous solution, 25° C., 24 hours | 0.05 |
| 7 | 50% methanol/aqueous solution, 25° C., 48 hours | Not detected |
| 8 | Water at 50° C., 24 hours | 0.02 |
| 9 | Water at 50° C., 48 hours | Not detected |
| 10 | Water at 50° C., stretching for 5 seconds | 1.2 |

As shown in Table 5, DMSO was difficult to remove by vacuum drying at 60° C. On the other hand, DMSO was removed efficiently by methanol, methanol/water, and hot water at 50° C. Films containing DMSO at an undetectable level can be used also as films compatible with the human body. Further, only by stretching the film in hot water, the amount of DMSO was reduced by about one-tenth.

Example 14

In this example, color film production was tested. First, 0.5 w/v % of each dye shown in Table 6 was added to DMSO, followed by dissolution at 60° C. for 2 hours while shaking, and further dissolution at 40° C. for 16 hours. The respective coloring solutions were added so that the concentration of the spider silk protein would be 5.98 mass %. Films were produced in the same manner as in Example 1. Table 6 shows the results.

TABLE 6

| No. | Dye | Result |
| --- | --- | --- |
| 1 | Acid dye: Acid Yellow RW New | A color film colored in bright yellow was obtained. |
| 2 | Acid dye: Acid Milling Sky Blue FSE | A color film colored in bright blue was obtained. |
| 3 | Acid dye: Polar Red B 125% | A color film colored in bright red was obtained. |
| 4 | Fluorescent dye: NKP-8315 Yellow | A color film colored in yellow fluorescence was obtained. When irradiated with ultraviolet light, the film emitted green fluorescence. |

Example 15

Unstretched films were produced in the same manner as in Example 1. One of the films obtained had a thickness of 69.0 μm and the other had a thickness of 10.1 μm. The unstretched films 30 mm in length and 30 mm in width were set at a Haze Meter (model HZ-2P, manufactured by Suga Test Instruments Co., Ltd.). Haze values of the respective films were measured using C light sources. The haze values were obtained from the following formula.

Haze rate [%]=($Td$ diffuse transmittance/$Tt$ total light transmittance)×100

The results of the measurement were as follows.

(1) Thickness: 69.0 μm, Td: 1.39, Tt: 91.65, Haze: 1.51 (%)

(2) Thickness: 10.1 μm, Td: 0.93, Tt: 92.5, Haze: 1(%)
From these results, it was confirmed that the unstretched films has high transparency.

INDUSTRIAL APPLICABILITY

The film of the present invention has favorable light transmittance and comparatively high refractive index, and hence is useful for an optical waveguide, an optical film containing a transparent conductive film, and the like. It also is useful as a color film.

Sequence Listing Free Text
SEQ ID NOS: 1-4 amino acid sequence
SEQ ID NOS: 5-7 base sequence
SEQ ID NOS: 8-11 primer sequence
SEQ ID NO: 12 amino acid sequence

The invention claimed is:

1. A method for producing a spider silk protein film containing a polypeptide derived from spider silk proteins, comprising:

dissolving a polypeptide derived from spider silk proteins in a dimethyl sulfoxide solvent to prepare a dope solution such that the dope solution consists essentially of the polypeptide derived from spider silk proteins and dimethyl sulfoxide (DMSO); and cast-molding the dope solution on a surface of a base to form the spider silk protein film.

2. The method for producing a spider silk protein film according to claim 1, wherein the dope solution has a viscosity of 15 to 80 centipoise (cP).

3. The method for producing a spider silk protein film according to claim 1, wherein the base to be used at the time of the cast molding is a polyethylene terephthalate (PET) film or a release film composed of a PET film and a silicone compound that is fixed on a surface of the PET film.

4. The method for producing a spider silk protein film according to claim 1, wherein the film is subjected to drying and/or desolvation by at least one selected from vacuum drying, hot-air drying, air drying, and immersion.

5. The method for producing a spider silk protein film according to claim 4, wherein the film after the drying and/or desolvation is stretched uniaxially or biaxially in water, or the film is subjected to desolvation simultaneously with stretching.

6. The method for producing a spider silk protein film according to claim 5, wherein the film after the stretching is subjected to thermal fixation by dry heat at 50 to 200° C.

7. The method for producing a spider silk protein film according to claim 1, further comprising:

dissolving or dispersing a colorant in DMSO to prepare a DMSO coloring liquid; and adding the DMSO coloring liquid to the dope solution or adding the dope solution to the DMSO coloring liquid and mixing them to prepare the dope solution for film casting.

* * * * *

UNITED STATES PATENT AND TRADEMARK OFFICE
CERTIFICATE OF CORRECTION

PATENT NO. : 11,306,126 B2
APPLICATION NO. : 16/371932
DATED : April 19, 2022
INVENTOR(S) : Sekiyama It is certified that error appears in the above-identified patent and that said Letters Patent is hereby corrected as shown below:

On the Title Page

Item (71), in Column 1, in "Applicant", delete "Tsuruoka" and insert -- Tsuruoka, Yamagata --.

Page 2, Item (56), in Column 2, under "Other Publications", Line 4, delete "Isoyanate," and insert -- Isocyanate, --.

Page 2, Item (56), in Column 2, under "Other Publications", Line 16, delete "Drageline" and insert -- Dragline --.

In the Specification

Column 4, Line 9, after "200°" insert -- C. --.

Column 5, Line 54, delete "REP 3" and insert -- REP3 --.

Column 6, Line 7, delete "REP 4" and insert -- REP4 --.

Column 9, Line 27, delete "Mao" and insert -- OD600 --.

Column 9, Line 30, delete "fmal" and insert -- final --.

Column 13, Line 19, delete "biaxcially" and insert -- biaxially --.

Signed and Sealed this
Ninth Day of August, 2022

Katherine Kelly Vidal
*Director of the United States Patent and Trademark Office*

SEQUENCE LISTING

```
<160> NUMBER OF SEQ ID NOS: 12

<210> SEQ ID NO 1
<211> LENGTH: 1154
<212> TYPE: PRT
<213> ORGANISM: Artificial
<220> FEATURE:
<223> OTHER INFORMATION: ADF3Kai-Large-NRSH1

<400> SEQUENCE: 1

Met His His His His His His His His Ser Ser Gly Ser Ser
1               5                   10                  15

Leu Glu Val Leu Phe Gln Gly Pro Ala Arg Ala Gly Ser Gly Gln Gln
                20                  25                  30

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
    290                 295                 300
```

Pro Gly Ser Gly Gln Gln Gly Pro Gly Gln Gln Gly Pro Gly Gln
305                 310                 315                 320

Gly Pro Tyr Gly Pro Gly Ala Ser Ala Ala Ala Ala Ala Gly Gly
            325                 330                 335

Tyr Gly Pro Gly Ser Gly Gln Gln Gly Pro Gly Gln Gln Gly Pro Gly
                340                 345                 350

Gln Gln Gly Pro Gly Gln Gln Gly Pro Gly Gln Gln Gly Pro Tyr Gly
            355                 360                 365

Pro Gly Ala Ser Ala Ala Ala Ala Ala Gly Gly Tyr Gly Pro Gly
        370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
        435                 440                 445

Gly Tyr Gly Pro Gly Ser Gly Gln Gln Gly Pro Gly Gln Gln Gly Pro
    450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
            485                 490                 495

Pro Gly Ala Ser Ala Ala Ala Ala Ala Gly Gly Tyr Gly Pro Gly
        500                 505                 510

Ser Gly Gln Gln Gly Pro Gly Gln Gln Gly Pro Gly Gln Gln Gly Pro
    515                 520                 525

Gly Gly Gln Gly Pro Tyr Gly Pro Gly Ala Ala Ser Ala Ala Val Ser
    530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
            565                 570                 575

Ala Ser Ala Ala Ala Ala Ala Gly Gly Tyr Gly Pro Gly Ser Gly
        580                 585                 590

Gln Gln Gly Pro Ser Gln Gly Pro Gly Gln Gln Gly Pro Gly Gly
        595                 600                 605

Gln Gly Pro Tyr Gly Pro Gly Ala Ser Ala Ala Ala Ala Ala Gly
        610                 615                 620

Gly Tyr Gly Pro Gly Ser Gly Gln Gln Gly Pro Gly Gln Gln Gly Pro
625                 630                 635                 640

Tyr Gly Pro Gly Ser Ser Ala Ala Ala Ala Ala Gly Gly Asn Gly
            645                 650                 655

Pro Gly Ser Gly Gln Gln Gly Ala Gly Gln Gln Gly Pro Gly Gln Gln
            660                 665                 670

Gly Pro Gly Ala Ser Ala Ala Ala Ala Ala Gly Gly Tyr Gly Pro
        675                 680                 685

Gly Ser Gly Gln Gln Gly Pro Gly Gln Gln Gly Pro Gly Gly Gln Gly
    690                 695                 700

Pro Tyr Gly Pro Gly Ala Ser Ala Ala Ala Ala Ala Gly Gly Tyr
705                 710                 715                 720

-continued

```
Gly Pro Gly Ser Gly Gln Gly Pro Gly Gln Gly Pro Gly Gln
            725                 730                 735

Gly Pro Tyr Gly Pro Gly Ala Ser Ala Ala Ala Ala Gly Gly
            740                 745                 750

Tyr Gly Pro Gly Ser Gly Gln Gln Gly Pro Gly Gln Gln Pro Gly
            755                 760                 765

Gln Gln Gly Pro Gly Gly Gln Gly Pro Tyr Gly Pro Gly Ala Ser Ala
        770                 775                 780

Ala Ala Ala Ala Ala Gly Gly Tyr Gly Pro Gly Tyr Gly Gln Gln Gly
785                 790                 795                 800

Pro Gly Gln Gln Gly Pro Gly Gln Gly Pro Tyr Gly Pro Gly Ala
            805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gln Gln Gly Pro Tyr Gly Pro
        835                 840                 845

Gly Ala Ser Ala Ala Ala Ala Ala Gly Gly Tyr Gly Pro Gly Ser
850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
            885                 890                 895

Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
            915                 920                 925

Gly Gln Gln Gly Pro Gly Gln Gln Gly Pro Gly Gln Gln Gly Pro Gly
930                 935                 940

Gln Gln Gly Pro Gly Gln Gln Gly Pro Gly Gly Gln Gly Ala Tyr Gly
945                 950                 955                 960

Pro Gly Ala Ser Ala Ala Ala Gly Ala Ala Gly Gly Tyr Gly Pro Gly
            965                 970                 975

Ser Gly Gln Gln Gly Pro Gly Gln Gln Gly Pro Gly Gln Gln Gly Pro
            980                 985                 990

Gly Gln Gln Gly Pro Gly Gln Gln Gly Pro Gly Gln Gln Gly Pro Gly
            995                1000                1005

Gln Gln Gly Pro Gly Gln Gln Gly Pro Tyr Gly Pro Gly Ala Ser
        1010                1015                1020

Ala Ala Ala Ala Ala Gly Gly Tyr Gly Pro Gly Ser Gly Gln
        1025                1030                1035

Gln Gly Pro Gly Gln Gln Gly Pro Gly Gln Gln Gly Pro Gly Gly
        1040                1045                1050

Gln Gly Pro Tyr Gly Pro Gly Ala Ala Ser Ala Ala Val Ser Val
        1055                1060                1065

Gly Gly Tyr Gly Pro Gln Ser Ser Ser Val Pro Val Ala Ser Ala
        1070                1075                1080

Val Ala Ser Arg Leu Ser Ser Pro Ala Ala Ser Ser Arg Val Ser
        1085                1090                1095

Ser Ala Val Ser Ser Leu Val Ser Ser Gly Pro Thr Lys His Ala
        1100                1105                1110

Ala Leu Ser Asn Thr Ile Ser Ser Val Val Ser Gln Val Ser Ala
        1115                1120                1125

Ser Asn Pro Gly Leu Ser Gly Cys Asp Val Leu Val Gln Ala Leu
```

-continued

```
                1130                1135                1140
        Leu Glu  Val Val Ser Ala Leu  Val Ser Ile Leu
                    1145                1150

<210> SEQ ID NO 2
<211> LENGTH: 660
<212> TYPE: PRT
<213> ORGANISM: Artificial
<220> FEATURE:
<223> OTHER INFORMATION: ADF3Kai

<400> SEQUENCE: 2

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
                100                 105                 110

Gly Gly Gln Gly Pro Tyr Gly Pro Gly Ser Ser Ala Ala Ala Ala
            115                 120                 125

Ala Gly Gly Asn Gly Pro Gly Ser Gln Gln Gly Ala Gly Gln Gln
            130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala
            210                 215                 220

Ala Ala Ala Gly Gly Tyr Gly Pro Gly Ser Gln Gln Gly Pro Gly
225                 230                 235                 240

Gln Gln Gly Pro Gly Gln Gln Gly Pro Gly Gln Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
            275                 280                 285

Tyr Gly Pro Gly Ala Ser Ala Ala Ser Ala Ala Ser Gly Gly Tyr Gly
            290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
            325                 330                 335

Tyr Gly Pro Gly Ser Gly Gln Gln Gly Pro Gly Gln Gln Gly Pro Gly
```

-continued

Gln Gln Gly Pro Gly Gln Gln Gly Pro Gly Gln Gln Gly Pro Tyr Gly
            340                 345                 350
                355                 360                 365

Pro Gly Ala Ser Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Gly Ala Ala Gly
            435                 440                 445

Gly Tyr Gly Pro Gly Ser Gly Gln Gln Gly Pro Gly Gln Gln Gly Pro
            450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
            515                 520                 525

Gly Gly Gln Gly Pro Tyr Gly Pro Gly Ala Ala Ser Ala Ala Val Ser
            530                 535                 540

Val Gly Gly Tyr Gly Pro Gln Ser Ser Val Pro Val Ala Ser Ala
545                 550                 555                 560

Val Ala Ser Arg Leu Ser Ser Pro Ala Ala Ser Ser Arg Val Ser Ser
                565                 570                 575

Ala Val Ser Ser Leu Val Ser Ser Gly Pro Thr Lys His Ala Ala Leu
            580                 585                 590

Ser Asn Thr Ile Ser Ser Val Val Ser Gln Val Ser Ala Ser Asn Pro
            595                 600                 605

Gly Leu Ser Gly Cys Asp Val Leu Val Gln Ala Leu Leu Glu Val Val
            610                 615                 620

Ser Ala Leu Val Ser Ile Leu Gly Ser Ser Ile Gly Gln Ile Asn
625                 630                 635                 640

Tyr Gly Ala Ser Ala Gln Tyr Thr Gln Met Val Gly Gln Ser Val Ala
                645                 650                 655

Gln Ala Leu Ala
            660

<210> SEQ ID NO 3
<211> LENGTH: 1183
<212> TYPE: PRT
<213> ORGANISM: Artificial
<220> FEATURE:
<223> OTHER INFORMATION: ADF3Kai-Large

<400> SEQUENCE: 3

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly

-continued

```
                35                  40                  45
Pro Tyr Gly Pro Gly Ala Ser Ala Ala Ala Ala Ala Gly Gly Tyr
 50                  55                  60
Gly Pro Gly Ser Gly Gln Gln Gly Pro Ser Gln Gln Gly Pro Gly Gln
 65                  70                  75                  80
Gln Gly Pro Gly Gly Gln Gly Pro Tyr Gly Pro Gly Ala Ser Ala Ala
                 85                  90                  95
Ala Ala Ala Ala Gly Gly Tyr Gly Pro Gly Ser Gly Gln Gln Gly Pro
                100                 105                 110
Gly Gly Gln Gly Pro Tyr Gly Pro Gly Ser Ser Ala Ala Ala Ala Ala
                115                 120                 125
Ala Gly Gly Asn Gly Pro Gly Ser Gly Gln Gln Gly Ala Gly Gln Gln
                130                 135                 140
Gly Pro Gly Gln Gln Gly Pro Gly Ala Ser Ala Ala Ala Ala Ala Ala
145                 150                 155                 160
Gly Gly Tyr Gly Pro Gly Ser Gly Gln Gln Gly Pro Gly Gln Gln Gly
                165                 170                 175
Pro Gly Gly Gln Gly Pro Tyr Gly Pro Gly Ala Ser Ala Ala Ala Ala
                180                 185                 190
Ala Ala Gly Gly Tyr Gly Pro Gly Ser Gly Gln Gln Pro Gly Gln Gln
                195                 200                 205
Gly Pro Gly Gly Gln Gly Pro Tyr Gly Pro Gly Ala Ser Ala Ala Ala
                210                 215                 220
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gly Gln Gly Pro Tyr Gly
                245                 250                 255
Pro Gly Ala Ser Ala Ala Ala Ala Ala Gly Gly Tyr Gly Pro Gly
                260                 265                 270
Tyr Gly Gln Gln Gly Pro Gly Gln Gln Gly Pro Gly Gln Gly Pro
                275                 280                 285
Tyr Gly Pro Gly Ala Ser Ala Ala Ser Ala Ala Ser Gly Gly Tyr Gly
                290                 295                 300
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Gly Gly
                325                 330                 335
Tyr Gly Pro Gly Ser Gly Gln Gln Gly Pro Gly Gln Gln Gly Pro Gly
                340                 345                 350
Gln Gln Gly Pro Gly Gln Gln Gly Pro Gly Gly Gln Gly Pro Tyr Gly
                355                 360                 365
Pro Gly Ala Ser Ala Ala Ala Ala Ala Gly Gly Tyr Gly Pro Gly
                370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
                405                 410                 415
Gln Gln Gly Pro Gly Gln Gln Gly Pro Gly Gln Gln Gly Pro Gly Gly
                420                 425                 430
Gln Gly Ala Tyr Gly Pro Gly Ala Ser Ala Ala Gly Ala Ala Gly
                435                 440                 445
Gly Tyr Gly Pro Gly Ser Gly Gln Gln Gly Pro Gly Gln Gln Gly Pro
                450                 455                 460
```

```
Gly Gln Gln Gly Pro Gly Gln Gln Gly Pro Gly Gln Gly Pro Gly
465                 470                 475                 480
Gln Gln Gly Pro Gly Gln Gln Gly Pro Gly Gln Gln Gly Pro Tyr Gly
                485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
        515                 520                 525
Gly Gly Gln Gly Pro Tyr Gly Pro Gly Ala Ala Ser Ala Ala Val Ser
    530                 535                 540
Val Ser Arg Ala Arg Ala Gly Ser Gly Gln Gln Gly Pro Gly Gln Gln
545                 550                 555                 560
Gly Pro Gly Gln Gln Gly Pro Gly Gln Gln Gly Pro Tyr Gly Pro Gly
                565                 570                 575
Ala Ser Ala Ala Ala Ala Ala Ala Gly Gly Tyr Gly Pro Gly Ser Gly
            580                 585                 590
Gln Gln Gly Pro Ser Gln Gln Gly Pro Gly Gln Gln Gly Pro Gly Gly
        595                 600                 605
Gln Gly Pro Tyr Gly Pro Gly Ala Ser Ala Ala Ala Ala Ala Ala Gly
    610                 615                 620
Gly Tyr Gly Pro Gly Ser Gly Gln Gln Gly Pro Gly Gly Gln Gly Pro
625                 630                 635                 640
Tyr Gly Pro Gly Ser Ser Ala Ala Ala Ala Ala Gly Gly Asn Gly
                645                 650                 655
Pro Gly Ser Gly Gln Gln Gly Ala Gln Gln Gly Pro Gly Gln Gln
            660                 665                 670
Gly Pro Gly Ala Ser Ala Ala Ala Ala Ala Gly Gly Tyr Gly Pro
        675                 680                 685
Gly Ser Gly Gln Gln Gly Pro Gly Gln Gln Gly Pro Gly Gln Gln Gly
    690                 695                 700
Pro Tyr Gly Pro Gly Ala Ser Ala Ala Ala Ala Ala Ala Gly Gly Tyr
705                 710                 715                 720
Gly Pro Gly Ser Gly Gln Gly Pro Gly Gln Gln Gly Pro Gly Gly Gln
                725                 730                 735
Gly Pro Tyr Gly Pro Gly Ala Ser Ala Ala Ala Ala Ala Ala Gly Gly
            740                 745                 750
Tyr Gly Pro Gly Ser Gly Gln Gln Gly Pro Gly Gln Gln Gly Pro Gly
        755                 760                 765
Gln Gln Gly Pro Gly Gly Gln Gly Pro Tyr Gly Pro Gly Ala Ser Ala
    770                 775                 780
Ala Ala Ala Ala Gly Gly Tyr Gly Pro Gly Tyr Gly Gln Gln Gly
785                 790                 795                 800
Pro Gly Gln Gln Gly Pro Gly Gln Gly Pro Tyr Gly Pro Gly Ala
                805                 810                 815
Ser Ala Ala Ser Ala Ala Ser Gly Gly Tyr Gly Pro Gly Ser Gly Gln
            820                 825                 830
Gln Gly Pro Gly Gln Gln Gly Pro Gly Gln Gln Gly Pro Tyr Gly Pro
        835                 840                 845
Gly Ala Ser Ala Ala Ala Ala Ala Ala Gly Gly Tyr Gly Pro Gly Ser
    850                 855                 860
Gly Gln Gln Gly Pro Gly Gln Gln Gly Pro Gly Gln Gln Gly Pro Gly
865                 870                 875                 880
```

```
Gln Gln Gly Pro Gly Gly Gln Gly Pro Tyr Gly Pro Gly Ala Ser Ala
            885                 890                 895

Ala Ala Ala Ala Ala Gly Gly Tyr Gly Pro Gly Ser Gly Gln Gln Gly
        900                 905                 910

Pro Gly Gln Gln Gly Pro Gly Gln Gln Gly Pro Gly Gln Gln Gly Pro
    915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gln Gln Gly Ala Tyr Gly
945                 950                 955                 960

Pro Gly Ala Ser Ala Ala Ala Gly Ala Ala Gly Gly Tyr Gly Pro Gly
            965                 970                 975

Ser Gly Gln Gln Gly Pro Gly Gln Gln Gly Pro Gly Gln Gln Gly Pro
        980                 985                 990

Gly Gln Gln Gly Pro Gly Gln Gln Gly Pro Gly Gln Gln Gly Pro Gly
        995                1000                1005

Gln Gln Gly Pro Gly Gln Gln Gly Pro Tyr Gly Pro Gly Ala Ser
    1010                1015                1020

Ala Ala Ala Ala Ala Ala Gly Gly Tyr Gly Pro Gly Ser Gly Gln
    1025                1030                1035

Gln Gly Pro Gly Gln Gln Gly Pro Gly Gln Gln Gly Pro Gly Gly
    1040                1045                1050

Gln Gly Pro Tyr Gly Pro Gly Ala Ala Ser Ala Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu Gly Ser Ser Ser
    1145                1150                1155

Ile Gly Gln Ile Asn Tyr Gly Ala Ser Ala Gln Tyr Thr Gln Met
    1160                1165                1170

Val Gly Gln Ser Val Ala Gln Ala Leu Ala
    1175                1180

<210> SEQ ID NO 4
<211> LENGTH: 24
<212> TYPE: PRT
<213> ORGANISM: Artificial
<220> FEATURE:
<223> OTHER INFORMATION: His tag and start codon

<400> SEQUENCE: 4

Met His His His His His His His His His Ser Ser Gly Ser Ser
1               5                   10                  15

Leu Glu Val Leu Phe Gln Gly Pro
            20

<210> SEQ ID NO 5
<211> LENGTH: 1983
```

<212> TYPE: DNA
<213> ORGANISM: Artificial
<220> FEATURE:
<223> OTHER INFORMATION: ADF3Kai

<400> SEQUENCE: 5

```
atgcatcacc atcatcatca tcaccaccac cattcctcgg gctcatcctt ggaagtgtta      60
tttcaaggac cagcacgagc cggttcggga caacaagggc ctggccagca gggcccaggt     120
caacaagggc caggacagca gggtccttat gggcccggcg caagcgcagc agctgcggcc     180
gctggtggct atggtcctgg ctccggtcaa cagggccctt cgcaacaagg tcccgggcag     240
caaggtcctg gtggccaggg tccctacggg ccggggggcga gtgcggcagc agccgctgca     300
ggcggttatg gtccaggaag cggacagcaa ggtccgggag gtcaaggtcc gtatggccca     360
ggctctagcg cggctgccgc tgccgcgggt ggcaacggac agggagcgg acaacagggc     420
gcgggacaac agggtccagg acagcaaggc ccaggggcgt cggcggctgc agcggcggcc     480
ggaggctatg acccggctc aggacaacag ggaccgggtc aacaaggacc cggtggccaa     540
ggcccctatg gcccgggcgc cagcgcggcc gcagccgccg cgggcgggta cggccccggt     600
agcgggccagg gaccaggtca gcaggggcca ggaggtcagg gcccatacgg tccgggcgca     660
tccgcggcgg cggcagcggc aggtggctac ggtcccggaa gcggccaaca ggggccaggg     720
caacaaggac caggacaaca aggtcctggg ggccaaggac cgtatggacc aggagcatca     780
gctgcagccg cggcagctgg cggttacggt ccaggctacg ccagcaggg tccgggtcag     840
cagggaccgg gaggccaggg gccttatggc cctggcgctt ccgcagccag tgccgcttct     900
ggaggatacg ggccgggaag cggtcagcaa ggccctggcc aacaaggacc tggaggccaa     960
gggccctacg gccaggagc ctcggcagcc gcagctgccg caggtgggta tgggccaggt    1020
agcgggcaac aagggccggg tcagcaagga ccggggcaac agggacctgg cagcaagga    1080
cccggggggtc aaggcccgta cggacctggt gcgtctgcag ctgctgctgc ggctggtgga    1140
tatggtccgg gatcggggca gcagggtccc ggtcagcagg ccctggtca gcaagggcca    1200
ggccaacagg gaccgggaca caaggcccg gtcaacagg gtcctggaca gcaggggccg    1260
ggccaacaag gccctgggca cagggtccg ggggacagg gggcctatgg gcctggcgca    1320
tctgccgccg ctggcgcagc cggtgggtac gggcctgggt caggtcaaca ggggcctggt    1380
caacaaggcc ccgggcaaca gggcccccggc cagcaaggtc cagggcagca gggcccggga    1440
cagcaagggc ctggacaaca gggggcccgga cagcagggac cttacgggcc cggtgcgagc    1500
gcagcggccg ccgccgcagg gggatatggc cccggatcgg gccagcaggg accaggccag    1560
caaggacctg gccaacaggg cccgggggggt caggggccgt atggtccggg cgctgcaagt    1620
gctgcagtgt ccgttggagg ttacggccct cagtcttcgt ctgttccggt ggcgtccgca    1680
gttgcgagta gactgtcttc acctgctgct tcatcgcgag tatcgagcgc tgtttcgtct    1740
cttgtctcgt cgggtcccac gaaacatgcc gccctttcaa atacgatttc atctgtagtg    1800
tcccaagtta gtgcaagtaa cccggggtta tccggatgcg acgttctcgt tcaggcactc    1860
ctagaagtag tatccgcgtt ggtgagcatc ttaggcagct cctcgatagg tcaaataaac    1920
tatggtgctt cagcccagta tacacagatg gtgggacaga gcgtcgcgca ggcattggct    1980
taa                                                                 1983
```

<210> SEQ ID NO 6
<211> LENGTH: 3552
<212> TYPE: DNA

<213> ORGANISM: Artificial
<220> FEATURE:
<223> OTHER INFORMATION: ADF3Kai-Large

<400> SEQUENCE: 6

| | | | | | |
|---|---|---|---|---|---|
| atgcatcacc | atcatcatca | tcaccaccac | cattcctcgg | gctcatcctt | ggaagtgtta | 60 |
| tttcaaggac | cagcacgagc | cggttcggga | caacaagggc | ctggccagca | gggcccaggt | 120 |
| caacaagggc | caggacagca | gggtccttat | gggcccggcg | caagcgcagc | agctgcggcc | 180 |
| gctggtggct | atggtcctgg | ctccggtcaa | cagggcccttt | cgcaacaagg | tcccgggcag | 240 |
| caaggtcctg | gtggccaggg | tccctacggg | ccggggcga | gtgcggcagc | agccgctgca | 300 |
| ggcggttatg | gtccaggaag | cggacagcaa | ggtccgggag | gtcaaggtcc | gtatggccca | 360 |
| ggctctagcg | cggctgccgc | tgccgcgggt | ggcaacggac | agggagcgg | acaacagggc | 420 |
| gcgggacaac | agggtccagg | acagcaaggc | ccaggggcgt | cggcggctgc | agcggcggcc | 480 |
| ggaggctatg | gacccggctc | aggacaacag | gaccgggtc | aacaaggacc | cggtggccaa | 540 |
| ggcccctatg | gcccgggcgc | cagcgcggcc | gcagccgccg | cggcgggta | cggcccggt | 600 |
| agcggccagg | gaccaggtca | gcaggggcca | ggaggtcagg | gcccatacgg | tccgggcgca | 660 |
| tccgcggcgg | cggcagcggc | aggtggctac | ggtcccggaa | gcggccaaca | ggggccaggg | 720 |
| caacaaggac | caggacaaca | aggtcctggg | ggccaaggac | cgtatggacc | aggagcatca | 780 |
| gctgcagccg | cggcagctgg | cggttacggt | ccaggctacg | gccagcaggg | tccgggtcag | 840 |
| cagggaccgg | gaggccaggg | gccttatggc | cctggcgctt | ccgcagccag | tgccgcttct | 900 |
| ggaggatacg | ggccgggaag | cggtcagcaa | ggccctggcc | aacaaggacc | tggaggccaa | 960 |
| gggccctacg | gcccaggagc | ctcggcagcc | gcagctgccg | caggtgggta | tgggccaggt | 1020 |
| agcgggcaac | aagggccggg | tcagcaagga | ccggggcaac | agggacctgg | gcagcaagga | 1080 |
| cccgggggtc | aaggcccgta | cggacctggt | gcgtctgcag | ctgctgctgc | ggctggtgga | 1140 |
| tatggtccgg | gatcggggca | gcagggtccc | ggtcagcagg | gcctggtca | gcaagggcca | 1200 |
| ggccaacagg | gacccggaca | caaggcccg | ggtcaacagg | gtcctggaca | gcaggggccg | 1260 |
| ggccaacaag | gccctgggca | acaggtccg | ggggacagg | gggcctatgg | gcctggcgca | 1320 |
| tctgccgccg | ctggcgcagc | cggtgggtac | gggcctgggt | caggtcaaca | ggggcctggt | 1380 |
| caacaaggcc | ccgggcaaca | ggggcccggc | cagcaaggtc | cagggcagca | gggcccggga | 1440 |
| cagcaagggc | ctggacaaca | ggggcccgga | cagcagggac | cttacgggcc | cggtgcgagc | 1500 |
| gcagcggccg | ccgccgcagg | gggatatggc | cccggatcgg | ccagcaggg | accaggccag | 1560 |
| caaggacctg | gccaacaggg | cccgggggggt | cagggggccgt | atggtccggg | cgctgcaagt | 1620 |
| gctgcagtgt | ccgtttctag | agcacgagcc | ggttcgggac | aacaagggcc | tggccagcag | 1680 |
| ggcccaggtc | aacaagggcc | aggacagcag | ggtccttatg | ggcccggcgc | aagcgcagca | 1740 |
| gctgcggccg | ctggtggcta | tggtcctggc | tccggtcaac | agggcccttc | gcaacaaggt | 1800 |
| cccgggcagc | aaggtcctgg | tggccaggt | ccctacgggc | cggggcgag | tgcggcagca | 1860 |
| gccgctgcag | gcggttatgg | tccaggaagc | ggacagcaag | gtccgggagg | tcaaggtccg | 1920 |
| tatggcccag | gctctagcgc | ggctgccgct | gccgcgggtg | gcaacggacc | agggagcgga | 1980 |
| caacagggcg | cgggacaaca | gggtccagga | cagcaaggcc | caggggcgtc | ggcggctgca | 2040 |
| gcggcggccg | gaggctatgg | acccggctca | ggacaacagg | gaccgggtca | acaaggaccc | 2100 |
| ggtggccaag | gcccctatgg | cccgggcgcc | agcgcggccg | cagccgccgc | gggcgggtac | 2160 |
| ggccccggta | gcggccaggg | accaggtcag | caggggccag | gaggtcaggg | cccatacggt | 2220 |

```
ccgggcgcat ccgcggcggc ggcagcggca ggtggctacg gtcccggaag cggccaacag    2280
gggccagggc aacaaggacc aggacaacaa ggtcctgggg gccaaggacc gtatggacca    2340
ggagcatcag ctgcagccgc ggcagctggc ggttacggtc caggctacgg ccagcagggt    2400
ccgggtcagc agggaccggg aggccagggg ccttatggcc ctggcgcttc cgcagccagt    2460
gccgcttctg gaggatacgg gccgggaagc ggtcagcaag ccctggcca acaaggacct    2520 ggaggccaag ggccctacgg cccaggagcc tcggcagccg cagctgccgc aggtgggtat    2580
gggccaggta gcgggcaaca agggccgggt cagcaaggac cggggcaaca gggacctggg    2640
cagcaaggac ccggggggtca aggcccgtac ggacctggtg cgtctgcagc tgctgctgcg    2700
gctggtggat atggtccggg atcggggcag cagggtcccg gtcagcaggg ccctggtcag    2760
caagggccag gccaacaggg acccggacaa caaggcccgg gtcaacaggg tcctggacag    2820
caggggccgg gccaacaagg ccctgggcaa cagggtccgg ggggacaggg ggcctatggg    2880
cctggcgcat ctgccgccgc tggcgcagcc ggtgggtacg ggcctgggtc aggtcaacag    2940
gggcctggtc aacaaggccc cggcaacag ggccccggcc agcaaggtcc agggcagcag    3000
ggcccgggac agcaagggcc tggacaacag gggcccggac agcagggacc ttacgggccc    3060
ggtgcgagcg cagcggccgc cgccgcaggg ggatatggcc ccggatcggg ccagcaggga    3120
ccaggccagc aaggacctgg ccaacagggc cggggggtc aggggccgta tggtcccggc    3180
gctgcaagtg ctgcagtgtc cgttggaggt tacggccctc agtcttcgtc tgttccggtg    3240
gcgtccgcag ttgcgagtag actgtcttca cctgctgctt catcgcgagt atcgagcgct    3300
gtttcgtctc ttgtctcgtc gggtcccacg aaacatgccg ccctttcaaa tacgatttca    3360
tctgtagtgt cccaagttag tgcaagtaac ccgggggttat ccggatgcga cgttctcgtt    3420
caggcactcc tagaagtagt atccgcgttg gtgagcatct taggcagctc ctcgataggt    3480
caaataaact atggtgcttc agcccagtat acacagatgg tgggacagag cgtcgcgcag    3540
gcattggctt aa                                                         3552
```

<210> SEQ ID NO 7
<211> LENGTH: 3465
<212> TYPE: DNA
<213> ORGANISM: Artificial
<220> FEATURE:
<223> OTHER INFORMATION: ADF3Kai-Large-NRSH1

<400> SEQUENCE: 7

```
atgcatcacc atcatcatca tcaccaccac cattcctcgg gctcatcctt ggaagtgtta      60
tttcaaggac cagcacgagc cggttcggga caacaagggc ctggccagca gggcccaggt     120
caacaagggc caggacagca gggtccttat gggcccggcg caagcgcagc agctgcggcc     180
gctggtggct atggtcctgg ctccggtcaa cagggccctt cgcaacaagg tcccgggcag     240
caaggtcctg gtggccaggg tccctacggg ccggggggcga gtgcggcagc agccgctgca     300
ggcggttatg gtccaggaag cggacagcaa ggtccgggag gtcaaggtcc gtatggccca     360
ggctctagcg cggctgccgc tgccgcgggt ggcaacggac cagggagcgg acaacagggc     420
gcgggacaac agggtccagg acagcaaggc cagggggcgt cggcggctgc agcggcggcc     480
ggaggctatg gacccggctc aggacaacag ggaccgggtc aacaaggacc cggtggccaa     540 ggccccctatg gccgggcgc cagcgcgcc cagccgccg cggcgggta cggcccggt        600 agcggccagg gaccaggtca gcaggggcca ggaggtcagg gcccatacgg tccgggcgca     660
```

```
tccgcggcgg cggcagcggc aggtggctac ggtcccggaa gcggccaaca ggggccaggg    720
caacaaggac caggacaaca aggtcctggg ggccaaggac cgtatggacc aggagcatca    780
gctgcagccg cggcagctgg cggttacggt ccaggctacg ccagcagggt ccgggtcag    840 cagggaccgg gaggccaggg gccttatggc cctggcgctt ccgcagccag tgccgcttct    900
ggaggatacg ggccgggaag cggtcagcaa ggccctggcc aacaaggacc tggaggccaa    960
gggccctacg gcccaggagc ctcggcagcc gcagctgccg caggtgggta tgggccaggt   1020
agcgggcaac aagggccggg tcagcaagga ccggggcaac agggacctgg gcagcaagga   1080
cccgggggtc aaggcccgta cggacctggt gcgtctgcag ctgctgctgc ggctggtgga   1140
tatggtccgg gatcggggca gcagggtccc ggtcagcagg gccctggtca gcaagggcca   1200
ggccaacagg gacccggaca caaggcccg gtcaacagg gtcctggaca gcaggggccg   1260
ggccaacaag gccctgggca caggtccg ggggacagg gggcctatgg gcctggcgca   1320
tctgccgccg ctggcgcagc cggtgggtac gggcctgggt caggtcaaca ggggcctggt   1380
caacaaggcc ccgggcaaca gggccccggc agcaaggtc cagggcagca gggcccggga   1440
cagcaagggc ctggacaaca ggggcccgga cagcagggac cttacgggcc cggtgcgagc   1500
gcagcggccg ccgccgcagg gggatatggc cccggatcgg ccagcaggg accaggccag   1560 caaggacctg gccaacaggg cccgggggg cagggggccgt atggtcccgg cgctgcaagt   1620
gctgcagtgt ccgtttctag agcacgagcc ggttcgggac aacaagggcc tggccagcag   1680
ggcccaggtc aacaagggcc aggacagcag gtccttatg ggcccggcgc aagcgcagca   1740
gctgcggccg ctggtggcta tggtcctggc tccggtcaac agggcccttc gcaacaaggt   1800
cccgggcagc aagtcctgg tggccagggt ccctacgggc cgggggcgag tgcggcagca   1860
gccgctgcag gcggttatgg tccaggaagc ggacagcaag gtccgggagg tcaaggtccg   1920
tatggcccag gctctagcgc ggctgccgct gccgcgggtg gcaacggacc agggagcgga   1980
caacagggcg cggacaaca gggtccagga cagcaaggcc caggggcgtc ggcggctgca   2040
gcggcggccg gaggctatgg acccggctca ggacaacagg gaccgggtca acaaggaccc   2100
ggtggccaag gccctatgg cccgggcgcc agcgcggccg cagccgccgc gggcgggtac   2160
ggccccggta gcggccaggg accaggtcag caggggccag gaggtcaggg cccatacggt   2220
ccgggcgcat ccgcggcggc ggcagcgca ggtggctacg gtcccggaag cggccaacag   2280
gggccagggc aacaaggacc aggacaacaa ggtcctgggg gccaaggacc gtatggacca   2340
ggagcatcag ctgcagccgc ggcagctggc ggttacggtc caggctacgg ccagcagggt   2400
ccgggtcagc agggaccggg aggccagggg ccttatggcc ctggcgcttc cgcagccagt   2460
gccgcttctg gaggatacgg gccgggaagc ggtcagcaag ccctggcca acaaggacct   2520 ggaggccaag ggccctacgg cccaggagcc tcggcagccg cagctgccgc aggtgggtat   2580
gggccaggta gcgggcaaca agggccgggt cagcaaggac cggggcaaca gggacctggg   2640
cagcaaggac ccgggggtca aggcccgtac ggacctggtg cgtctgcagc tgctgctgcg   2700
gctggtggat atggtccggg atcggggcag cagggtcccg gtcagcaggg ccctggtcag   2760
caagggccag gccaacaggg acccggacaa caaggcccgg gtcaacaggg tcctggacag   2820
caggggccgg gccaacaagg ccctgggcaa cagggtccgg ggggacaggg ggcctatggg   2880
cctggcgcat ctgccgccgc tggcgcagcc ggtgggtacg ggcctgggtc aggtcaacag   2940
gggcctggtc aacaaggccc cgggcaacag ggccccggcc agcaaggtcc agggcagcag   3000
ggcccgggac agcaagggcc tggacaacag gggcccggac agcagggacc ttacgggccc   3060
```

```
ggtgcgagcg cagcggccgc cgccgcaggg ggatatggcc ccggatcggg ccagcaggga    3120
ccaggccagc aaggacctgg ccaacagggc ccggggggtc aggggccgta tggtcccggc    3180
gctgcaagtg ctgcagtgtc cgttggaggt tacggccctc agtcttcgtc tgttccggtg    3240
gcgtccgcag ttgcgagtag actgtcttca cctgctgctt catcgcgagt atcgagcgct    3300
gtttcgtctc ttgtctcgtc gggtcccacg aaacatgccg ccctttcaaa tacgatttca    3360
tctgtagtgt cccaagttag tgcaagtaac ccggggttat ccggatgcga cgttctcgtt    3420
caggcactcc tagaagtagt atccgcgttg gtgagcatct tataa                   3465
```

```
<210> SEQ ID NO 8
<211> LENGTH: 20
<212> TYPE: DNA
<213> ORGANISM: Artificial
<220> FEATURE:
<223> OTHER INFORMATION: T7 promoter primer

<400> SEQUENCE: 8
taatacgact cactataggg                                                  20

<210> SEQ ID NO 9
<211> LENGTH: 27
<212> TYPE: DNA
<213> ORGANISM: Artificial
<220> FEATURE:
<223> OTHER INFORMATION: Rep Xba I primer

<400> SEQUENCE: 9
tctagaaacg gacactgcag cacttgc                                          27

<210> SEQ ID NO 10
<211> LENGTH: 28
<212> TYPE: DNA
<213> ORGANISM: Artificial
<220> FEATURE:
<223> OTHER INFORMATION: Xba I Rep primer

<400> SEQUENCE: 10
tctagagcac gagccggttc gggacaac                                         28

<210> SEQ ID NO 11
<211> LENGTH: 19
<212> TYPE: DNA
<213> ORGANISM: Artificial
<220> FEATURE:
<223> OTHER INFORMATION: T7 terminator primer

<400> SEQUENCE: 11
gctagttatt gctcagcgg                                                   19

<210> SEQ ID NO 12
<211> LENGTH: 5
<212> TYPE: PRT
<213> ORGANISM: Artificial
<220> FEATURE:
<221> NAME/KEY: VARIANT
<222> LOCATION: 5
<223> OTHER INFORMATION: Nephila clavipes flagelliform silk Ala Ser Tyr
      Val

<400> SEQUENCE: 12

Gly Pro Gly Gly Xaa
1               5
```